(12) United States Patent
Tenmizu et al.

(10) Patent No.: US 7,399,587 B2
(45) Date of Patent: Jul. 15, 2008

(54) CANINE CYP1A2 GENETIC POLYMORPHISM

(75) Inventors: Daisuke Tenmizu, Tokyo (JP); Yasuhisa Fukunaga, Tokyo (JP); Kiyoshi Noguchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 104 days.

(21) Appl. No.: 10/536,809

(22) PCT Filed: May 28, 2004

(86) PCT No.: PCT/JP2004/007356

§ 371 (c)(1), (2), (4) Date: May 27, 2005

(87) PCT Pub. No.: WO2004/106521

PCT Pub. Date: Dec. 9, 2004

(65) Prior Publication Data

US 2006/0051766 A1    Mar. 9, 2006

(30) Foreign Application Priority Data

May 29, 2003  (JP)  ............................. 2003-152917
Aug. 7, 2003   (JP)  ............................. 2003-206581

(51) Int. Cl.
*C07H 21/04* (2006.01)
*C12Q 1/68* (2006.01)

(52) U.S. Cl. .................... 435/6; 435/91.1; 435/91.2; 536/23.1; 536/24.3

(58) Field of Classification Search ............... None
See application file for complete search history.

(56) References Cited

FOREIGN PATENT DOCUMENTS

EP          0 873 998       10/1998
WO       WO 96/16172       5/1996

OTHER PUBLICATIONS

Mise (Pharmacogenetics, vol. 14, pp. 769-773, Nov. 2004).*
Tacher et al. (J. of Heredity, vol. 96, No. 7, pp. 812-816, 2005).*
Uchida et al. (Molecular Pharmacology, vol. 38, pp. 644-651, 1990).*
Translation of International Preliminary Report on Patentability, for PCT Application No. PCT/JP2004/007356, filed May 28, 2004.
Supplementary Partial European Search Report dated Aug. 16, 2006, for EP Application No. 04745392.3.
Azuma et al., "Comparative Analysis of In Vitro and In Vivo Pharmacokinetic Parameters Related to Individual Variability of GTS-21 in Canine," Drug Metabol. Pharmacokin., 17(1): 75-82 (2002).
Mise et al., "Polymorphic Expression of CYP1A2 Leading to Interindividual Variability in Metabolism of a Novel Benzodiazepine Receptor Partial Inverse Agonist in Dogs," Drug Metabolism and Disposition, 32:240-245 (2004).
Mise et al., "Identification of Non-functional Allelic Variant of *CYP1A2* in Dogs," Pharmacogenetics, 14:769-773 (2004).
Tenmizu et al., "Identification of the Novel Canine CYP1A2 1117 C>T SNP Causing Protein Deletion," Xenobiotica, 34(9): 835-846 (2004).
Nagata et al., "Genetic Polymorphism of Human Cytochrome P450 Involved in Drug Metabolism," *Drug Metabol. Pharmacokin.*, 17(3):167-189 (2002).
Uchida et al, "Isolation of cDNAs Coding for Three Different Forms of Liver Microsomal Cytochrome P-450 from Polychlorinated Biphenyl-Treated Beagle Dogs," *Molecular Pharmacology*, 38:644-651 (1990).
Office Action dated Nov. 30, 2007, in Canadian Application No. 2,511,404 for "Canine CYP1A2 Gene Polymorphism."

* cited by examiner

*Primary Examiner*—Jeanine A Goldberg
(74) *Attorney, Agent, or Firm*—Finnegan, Henderson, Farabow, Garrett, & Dunner, LLP

(57) ABSTRACT

Disclosed is a method for determining whether a dog is an extensive metabolizer or a poor metabolizer in the rate of drug metabolism, by preparing a DNA sample from a dog, and determining a base corresponding to a base at position 1117 of a canine CYP1A2 gene (i.e., at position 87 of exon 4). According to the method, a CYP1A2 gene diagnosis of dogs (particularly beagles) used in a pharmacological effect test or a toxicity test can be rapidly carried out prior to the test, and thus the dogs can be easily divided into a group having a normal metabolic ability (an extensive metabolizer group) and a group having a low metabolic ability (a poor metabolizer group).

4 Claims, 1 Drawing Sheet

```
                        SEQUENCE LISTING

<160> NUMBER OF SEQ ID NOS: 23

<210> SEQ ID NO 1
<211> LENGTH: 1380
<212> TYPE: DNA
<213> ORGANISM: Canis familiaris
<220> FEATURE:
<223> OTHER INFORMATION: Inventor: Tenmizu, Daisuke; Fukunaga, Yasuhisa;
      Noguchi, Kiyoshi

<400> SEQUENCE: 1
ctggagtctt atgtaccttg tggcaaaccc tgagatacag agaaagatcc agaaggagtt      60
gggtatgcgg tagagatgca caagctaaga gaagcttgag atccccaggt tctttgttca    120
atgacatata gctgttgtgt gcctaccatg tgtaagccct gggcatacac tggtgcccac    180
ccttgcctag aacatgctgg ggtagggtgg ttactgggcc ttagatatat aacagacagt    240
actatgtaat aggggactta gataccatga agcagtcggg gcagccctaa gcccggtttg    300
```

```
gtcttctgtg ttctgcagac acggtgattg gcagggcacg gcagcctcgc ctctctgaca    360
ggccccagct gcccttaatg gaggccttca tcctggagat cttctgacac acctccttta    420
tccccttcac catccccac aggtaaggcc tgcttcttct gccttgccac ctttgtagcc     480
ttcaccatgt ttcttcctcc catcttctca gccctggatc tggctcagac ctcggcctct    540
cacttctggc cacgtcacca agttcccctc agcctcttgg ctgccgacaa ccaatccaac    600
catgatcaaa ctacccagct ttcaggagaa agtcacactg ctgatctcag ctctcattca    660
cctctgctca cattcctttc ctgcaagtac tctcaatcca cccgggctgg cctcgctgta    720 cctcccagc atgatgcggt caacctccaa ttttgcttat gctggacctt ctgcctggaa     780
tgccttttaa cctcttctcc caccacctga atcttaccct tgcccaaggt caatcctgac    840
acaaacttcc ccttcactat caggctttct tgactcatcc agctggcaca gcttcattct    900
ctgatgtatt gtaggacttt cagccatttg tccttgatca tgtcctgggc ttttaacaac    960
atcaagagac ttagtgaaca tttactctta cccatatgtt ggtctattta ttcccagagt   1020
agaaggtctg actcctcagt caggctggga actacccagg gatactccag actgccagtt   1080
tcttggcttc agaggatggc gaagtgcaca gctggacaca aacaaaggtt tagtgaacac   1140
ttgctgaagt tgaagaacag aagctgagga agaggaagga tagtttcacc ccttccgtgc   1200
tcctgatagt ccctcccagt gtaggacata gagactgtgg gggacaagct attggggtgg   1260
aagaaggagc aagtagatcc cagagacaca ccccagtgtt cctgccctga gctgacaga    1320 gccctcttcc ctcctcagca caacaaagga cacaacctta aagggcttct acatccccaa   1380

<210> SEQ ID NO 2
<211> LENGTH: 20
<212> TYPE: DNA
<213> ORGANISM: Canis familiaris

<400> SEQUENCE: 2
cctccaccat cttctgcttg                                                   20

<210> SEQ ID NO 3
<211> LENGTH: 20
<212> TYPE: DNA
<213> ORGANISM: Canis familiaris

<400> SEQUENCE: 3
atgtcctgga cactgcgctc                                                   20

<210> SEQ ID NO 4
<211> LENGTH: 20
<212> TYPE: DNA
<213> ORGANISM: Canis familiaris

<400> SEQUENCE: 4
tccccctcct aatgagctcc                                                   20

<210> SEQ ID NO 5
<211> LENGTH: 20
<212> TYPE: DNA
<213> ORGANISM: Canis familiaris

<400> SEQUENCE: 5
gaggccatgg gtgatccttc                                                   20

<210> SEQ ID NO 6
```

```
<211> LENGTH: 20
<212> TYPE: DNA
<213> ORGANISM: Canis familiaris

<400> SEQUENCE: 6
cctccaccat cttctgcttg                                                    20

<210> SEQ ID NO 7
<211> LENGTH: 20
<212> TYPE: DNA
<213> ORGANISM: Canis familiaris

<400> SEQUENCE: 7
caatgacatt ggccactgac                                                    20

<210> SEQ ID NO 8
<211> LENGTH: 20
<212> TYPE: DNA
<213> ORGANISM: Canis familiaris

<400> SEQUENCE: 8
tttggggccg gatttgacac                                                    20

<210> SEQ ID NO 9
<211> LENGTH: 20
<212> TYPE: DNA
<213> ORGANISM: Canis familiaris

<400> SEQUENCE: 9
gaggccatgg gtgatccttc                                                    20

<210> SEQ ID NO 10
<211> LENGTH: 18
<212> TYPE: DNA
<213> ORGANISM: Canis familiaris

<400> SEQUENCE: 10
ctggagtctt atgtacct                                                      18

<210> SEQ ID NO 11
<211> LENGTH: 18
<212> TYPE: DNA
<213> ORGANISM: Canis familiaris

<400> SEQUENCE: 11
ccactggttt atgaagac                                                      18

<210> SEQ ID NO 12
<211> LENGTH: 19
<212> TYPE: DNA
<213> ORGANISM: Canis familiaris

<400> SEQUENCE: 12
tgcccttaat ggaggcctt                                                     19

<210> SEQ ID NO 13
<211> LENGTH: 20
<212> TYPE: DNA
<213> ORGANISM: Canis familiaris

<400> SEQUENCE: 13
acgacacccc ctaccacttc                                                    20
```

```
<210> SEQ ID NO 14
<211> LENGTH: 20
<212> TYPE: DNA
<213> ORGANISM: Canis familiaris

<400> SEQUENCE: 14
ttcatcctgg agatcttccg                                              20

<210> SEQ ID NO 15
<211> LENGTH: 20
<212> TYPE: DNA
<213> ORGANISM: Canis familiaris

<400> SEQUENCE: 15
aattggaggt tgaccgcatc                                              20

<210> SEQ ID NO 16
<211> LENGTH: 20
<212> TYPE: DNA
<213> ORGANISM: Canis familiaris

<400> SEQUENCE: 16
ttcatcctgg agatcttctg                                              20

<210> SEQ ID NO 17
<211> LENGTH: 20
<212> TYPE: DNA
<213> ORGANISM: Canis familiaris

<400> SEQUENCE: 17
cccggtttgg tcttctgtgt                                              20

<210> SEQ ID NO 18
<211> LENGTH: 20
<212> TYPE: DNA
<213> ORGANISM: Canis familiaris

<400> SEQUENCE: 18
tgacgtggcc agaagtgaga                                              20

<210> SEQ ID NO 19
<211> LENGTH: 44
<212> TYPE: RNA
<213> ORGANISM: Artificial Sequence
<220> FEATURE:
<223> OTHER INFORMATION: Description of Artificial Sequence: an
      artificially synthesized GeneRacer RNA Oligo

<400> SEQUENCE: 19
cgacuggagc acgaggacac ugacauggac ugaaggagua gaaa                   44

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: an
      artificially synthesized GeneRacer 5' primer

<400> SEQUENCE: 20
cgactggagc acgaggacac tga                                          23

<210> SEQ ID NO 21
<211> LENGTH: 24
<212> TYPE: DNA
```

-continued

```
<213> ORGANISM: Canis familiaris

<400> SEQUENCE: 21
ggactcttca ggcctttggg aagc                                            24

<210> SEQ ID NO 22
<211> LENGTH: 1638
<212> TYPE: DNA
<213> ORGANISM: Canis familiaris
<220> FEATURE:
<221> NAME/KEY: CDS
<222> LOCATION: (63)..(1601)
<223> OTHER INFORMATION:

<400> SEQUENCE: 22
agctctgtac cagcctccac aatcctactg atctcaagct cctgcctcta cagttgatac    60 ag atg gca ttg tcc cag atg gcc aca gag ctt ctc ctg gcc tcc acc      107
   Met Ala Leu Ser Gln Met Ala Thr Glu Leu Leu Leu Ala Ser Thr
   1               5                  10                  15 atc ttc tgc ttg gta ctc tgg gtg gtc aag gcc tgg cag cct cgg ctt    155
Ile Phe Cys Leu Val Leu Trp Val Val Lys Ala Trp Gln Pro Arg Leu
                20                  25                  30 ccc aaa ggc ctg aag agt cca ccg ggg ccc tgg ggc tgg ccc ctg ctc    203
Pro Lys Gly Leu Lys Ser Pro Pro Gly Pro Trp Gly Trp Pro Leu Leu
            35                  40                  45 ggg aac gtg ctg acc ttg ggc aag agc ccc cac ctg gcg ctg tcc agg    251
Gly Asn Val Leu Thr Leu Gly Lys Ser Pro His Leu Ala Leu Ser Arg
        50                  55                  60 ctg agc cag cgt tat ggg gac gtg ctg cag atc cgc atc ggc tcc acc    299
Leu Ser Gln Arg Tyr Gly Asp Val Leu Gln Ile Arg Ile Gly Ser Thr
    65                  70                  75 ccc gtg ctg gtg ctc agt ggc ctg gac acc atc cgg cag gcc ctg gtg    347
Pro Val Leu Val Leu Ser Gly Leu Asp Thr Ile Arg Gln Ala Leu Val
80                  85                  90                  95 cgc cag ggg gat gat ttc aag ggc cgg ccc gac ctc tac agc ttc tct    395
Arg Gln Gly Asp Asp Phe Lys Gly Arg Pro Asp Leu Tyr Ser Phe Ser
                100                 105                 110 ctg gtg acc gac ggc caa agc ctg acc ttc agc cca gac tcc gga cca    443
Leu Val Thr Asp Gly Gln Ser Leu Thr Phe Ser Pro Asp Ser Gly Pro
            115                 120                 125 gtg tgg gct gcg cgc agg cgc ctg gct cag aac gcg ctc aac acc ttc    491
Val Trp Ala Ala Arg Arg Arg Leu Ala Gln Asn Ala Leu Asn Thr Phe
        130                 135                 140 tcc att gcc tcc gac ccg gct tcc tcg tgc tct tgc tac ctg gaa gag    539
Ser Ile Ala Ser Asp Pro Ala Ser Ser Cys Ser Cys Tyr Leu Glu Glu
    145                 150                 155 cat gtg agc aag gag gcc gag gcc ctt ctc agc agg ctg cag gag cag    587
His Val Ser Lys Glu Ala Glu Ala Leu Leu Ser Arg Leu Gln Glu Gln
160                 165                 170                 175 atg gca gag gtt ggg cgc ttt gat ccc tac aac caa gtg ctg atg tca    635
Met Ala Glu Val Gly Arg Phe Asp Pro Tyr Asn Gln Val Leu Met Ser
                180                 185                 190 gtg gcc aat gtc att ggt gca atg tgc ttt ggg cac cac ttc tct cag    683
Val Ala Asn Val Ile Gly Ala Met Cys Phe Gly His His Phe Ser Gln
            195                 200                 205 aga agt gag gaa atg ctc ccc ctc cta atg agc tcc agt gat ttt gtg    731
Arg Ser Glu Glu Met Leu Pro Leu Leu Met Ser Ser Ser Asp Phe Val
        210                 215                 220 gag acc gtc tcc aac ggg aac ccg gtg gac ttt ttc ccc att ctc caa    779
Glu Thr Val Ser Asn Gly Asn Pro Val Asp Phe Phe Pro Ile Leu Gln
    225                 230                 235
```

```
tat atg ccc aac tca gcc ctg cag aga ttc aag aac ttc aac cag acg    827
Tyr Met Pro Asn Ser Ala Leu Gln Arg Phe Lys Asn Phe Asn Gln Thr
240                 245                 250                 255 ttc gtg cag tcc ctg cag aaa att gtc cag gaa cac tat caa gac ttt    875
Phe Val Gln Ser Leu Gln Lys Ile Val Gln Glu His Tyr Gln Asp Phe
                260                 265                 270 gat gag cgc agt gtc cag gac atc aca ggc gcc ctc ttg aag cac aat    923
Asp Glu Arg Ser Val Gln Asp Ile Thr Gly Ala Leu Leu Lys His Asn
            275                 280                 285 gag aag agc tcc agg gct agt gat ggc cac atc ccc caa gag aag att    971
Glu Lys Ser Ser Arg Ala Ser Asp Gly His Ile Pro Gln Glu Lys Ile
        290                 295                 300 gtc aac ctt atc aac gac att ttt ggg gcc gga ttt gac act gtc aca   1019
Val Asn Leu Ile Asn Asp Ile Phe Gly Ala Gly Phe Asp Thr Val Thr
    305                 310                 315 acg gcc att tcc tgg agt ctt atg tac ctt gtg gca aac cct gag ata   1067
Thr Ala Ile Ser Trp Ser Leu Met Tyr Leu Val Ala Asn Pro Glu Ile
320                 325                 330                 335 cag aga aag atc cag aag gag ttg gac acg gtg att ggc agg gca cgg   1115
Gln Arg Lys Ile Gln Lys Glu Leu Asp Thr Val Ile Gly Arg Ala Arg
                340                 345                 350 cag cct cgc ctc tct gac agg ccc cag ctg ccc tta atg gag gcc ttc   1163
Gln Pro Arg Leu Ser Asp Arg Pro Gln Leu Pro Leu Met Glu Ala Phe
            355                 360                 365 atc ctg gag atc ttc cga cac acc tcc ttt gtc ccc ttc acc atc ccc   1211
Ile Leu Glu Ile Phe Arg His Thr Ser Phe Val Pro Phe Thr Ile Pro
        370                 375                 380 cac agc aca aca aag gac aca acc tta aag ggc ttc tac atc ccc aag   1259
His Ser Thr Thr Lys Asp Thr Thr Leu Lys Gly Phe Tyr Ile Pro Lys
    385                 390                 395 gaa tgc tgt gtc ttc ata aac cag tgg cag gtc aat cat gac caa sag   1307
Glu Cys Cys Val Phe Ile Asn Gln Trp Gln Val Asn His Asp Gln Xaa
400                 405                 410                 415 gtg tgg ggg gat cca ttt gca ttc cgg cca gag cga ttc ctc act gca   1355
Val Trp Gly Asp Pro Phe Ala Phe Arg Pro Glu Arg Phe Leu Thr Ala
                420                 425                 430 gat ggy acc rcc atc aac aag acc ttg agt gag aag gtg atg ctc ttt   1403
Asp Xaa Thr Xaa Ile Asn Lys Thr Leu Ser Glu Lys Val Met Leu Phe
            435                 440                 445 ggc atg ggc aag cgc cgg tgc ata gga gag gtc ctg gcc aag tgg gag   1451
Gly Met Gly Lys Arg Arg Cys Ile Gly Glu Val Leu Ala Lys Trp Glu
        450                 455                 460 atc ttc ctc ttc cta gcc atc ttg ctg cag cgg ctg gag ttc agc gtg   1499
Ile Phe Leu Phe Leu Ala Ile Leu Leu Gln Arg Leu Glu Phe Ser Val
    465                 470                 475 cca gca ggt gtg aaa gta gac cta acc ccc atc tat ggg ctg acc atg   1547
Pro Ala Gly Val Lys Val Asp Leu Thr Pro Ile Tyr Gly Leu Thr Met
480                 485                 490                 495 aag cac acc cgc tgt gag cat gtc cag gca cgg cca cgc ttc tcc atc   1595
Lys His Thr Arg Cys Glu His Val Gln Ala Arg Pro Arg Phe Ser Ile
                500                 505                 510 aag tga aggcaccagc atgycaaggc agagggagga gaaggat                  1638
Lys

<210> SEQ ID NO 23
<211> LENGTH: 512
<212> TYPE: PRT
<213> ORGANISM: Canis familiaris
<220> FEATURE:
<221> NAME/KEY: misc_feature
```

```
<222> LOCATION: (415)..(415)
<223> OTHER INFORMATION: The 'Xaa' at location 415 stands for Glu or
      Gln.
<220> FEATURE:
<221> NAME/KEY: misc_feature
<222> LOCATION: (433)..(433)
<223> OTHER INFORMATION: The 'Xaa' at location 433 stands for Gly.
<220> FEATURE:
<221> NAME/KEY: misc_feature
<222> LOCATION: (435)..(435)
<223> OTHER INFORMATION: The 'Xaa' at location 435 stands for Ala or
      Thr.

<400> SEQUENCE: 23

Met Ala Leu Ser Gln Met Ala Thr Glu Leu Leu Ala Ser Thr Ile
 1               5                  10                  15

Phe Cys Leu Val Leu Trp Val Val Lys Ala Trp Gln Pro Arg Leu Pro
                20                  25                  30

Lys Gly Leu Lys Ser Pro Pro Gly Pro Trp Gly Trp Pro Leu Leu Gly
            35                  40                  45

Asn Val Leu Thr Leu Gly Lys Ser Pro His Leu Ala Leu Ser Arg Leu
        50                  55                  60

Ser Gln Arg Tyr Gly Asp Val Leu Gln Ile Arg Ile Gly Ser Thr Pro
65                  70                  75                  80

Val Leu Val Leu Ser Gly Leu Asp Thr Ile Arg Gln Ala Leu Val Arg
                85                  90                  95

Gln Gly Asp Asp Phe Lys Gly Arg Pro Asp Leu Tyr Ser Phe Ser Leu
            100                 105                 110

Val Thr Asp Gly Gln Ser Leu Thr Phe Ser Pro Asp Ser Gly Pro Val
        115                 120                 125

Trp Ala Arg Arg Arg Leu Ala Gln Asn Ala Leu Asn Thr Phe Ser
130                 135                 140

Ile Ala Ser Asp Pro Ala Ser Ser Cys Ser Cys Tyr Leu Glu His
145                 150                 155                 160

Val Ser Lys Glu Ala Glu Ala Leu Leu Ser Arg Leu Gln Glu Gln Met
                165                 170                 175

Ala Glu Val Gly Arg Phe Asp Pro Tyr Asn Gln Val Leu Met Ser Val
            180                 185                 190

Ala Asn Val Ile Gly Ala Met Cys Phe Gly His His Phe Ser Gln Arg
        195                 200                 205

Ser Glu Glu Met Leu Pro Leu Leu Met Ser Ser Asp Phe Val Glu
210                 215                 220

Thr Val Ser Asn Gly Asn Pro Val Asp Phe Phe Pro Ile Leu Gln Tyr
225                 230                 235                 240

Met Pro Asn Ser Ala Leu Gln Arg Phe Lys Asn Phe Asn Gln Thr Phe
                245                 250                 255

Val Gln Ser Leu Gln Lys Ile Val Gln Glu His Tyr Gln Asp Phe Asp
            260                 265                 270

Glu Arg Ser Val Gln Asp Ile Thr Gly Ala Leu Leu Lys His Asn Glu
        275                 280                 285

Lys Ser Ser Arg Ala Ser Asp Gly His Ile Pro Gln Glu Lys Ile Val
    290                 295                 300

Asn Leu Ile Asn Asp Ile Phe Gly Ala Gly Phe Asp Thr Val Thr Thr
305                 310                 315                 320

Ala Ile Ser Trp Ser Leu Met Tyr Leu Val Ala Asn Pro Glu Ile Gln
                325                 330                 335

Arg Lys Ile Gln Lys Glu Leu Asp Thr Val Ile Gly Arg Ala Arg Gln
```

-continued

```
            340                 345                 350
Pro Arg Leu Ser Asp Arg Pro Gln Leu Pro Leu Met Glu Ala Phe Ile
        355                 360                 365

Leu Glu Ile Phe Arg His Thr Ser Phe Val Pro Phe Thr Ile Pro His
        370                 375                 380

Ser Thr Thr Lys Asp Thr Thr Leu Lys Gly Phe Tyr Ile Pro Lys Glu
385                 390                 395                 400

Cys Cys Val Phe Ile Asn Gln Trp Gln Val Asn His Asp Gln Xaa Val
                405                 410                 415

Trp Gly Asp Pro Phe Ala Phe Arg Pro Glu Arg Phe Leu Thr Ala Asp
            420                 425                 430

Xaa Thr Xaa Ile Asn Lys Thr Leu Ser Glu Lys Val Met Leu Phe Gly
        435                 440                 445

Met Gly Lys Arg Arg Cys Ile Gly Glu Val Leu Ala Lys Trp Glu Ile
    450                 455                 460

Phe Leu Phe Leu Ala Ile Leu Leu Gln Arg Leu Glu Phe Ser Val Pro
465                 470                 475                 480

Ala Gly Val Lys Val Asp Leu Thr Pro Ile Tyr Gly Leu Thr Met Lys
            485                 490                 495

His Thr Arg Cys Glu His Val Gln Ala Arg Pro Arg Phe Ser Ile Lys
                500                 505                 510
```

CANINE CYP1A2 GENETIC POLYMORPHISM

TECHNICAL FIELD

The present invention relates to a detection of individual variations in drug metabolism by determining a single nucleotide polymorphism (hereinafter referred to as SNP) in a CYP1A2 gene of a dog (particularly a beagle) used in a medicament test, a method for selecting a dog used in a medicament test, and a DNA for determining a sequence of a polymorphic region.

BACKGROUND ART

Drug metabolism is a change in a chemical structure of a compound caused by an enzymatic action in a living body. Such an enzym, contributing to drug metabolism, is called a drug metabolizing enzyme. Drug metabolizing enzymes are considered originally to catalyze synthetic reactions or decomposition reactions of biomolecules such as steroids, fatty acids, or bile acids, but can metabolize drugs administered to or invading the body (i.e., foreign substances), whereby the foreign substances are eliminated from the body.

A drug metabolizing reaction is basically composed of a phase I reaction and a phase II reaction. In the phase I reaction, one or more polar functional groups are introduced to a drug by oxidation, reduction, and/or hydrolysis. In the phase II reaction, one or more biomolecules such as glucuronic acid, sulfuric acid, or glutathione are bound to the functional group(s) generated in the phase I reaction. The phase I and phase II reactions impart an excellent water-solubility to the drug, and as a result, the drug is easily excreted from the body.

Metabolizing enzymes contributing to approximately 80% of all phase I drug metabolizing reactions are called "cytochrome P450" (hereinafter referred to as "CYP"). CYPs have a molecular weight of approximately 50000 and contain a protoheme as a prosthetic group. When an average molecular weight of an amino acid is regarded as 100, CYP is composed of approximately 500 amino acids. In the classification and nomenclature of CYPs, CYPs are systematically denoted by placing an Arabic numeral indicating a "family" and an alphabetic character indicating a "subfamily" after "CYP". A group of CYP molecules showing a homology (amino acid sequence) of more than 40% is regarded as a family. A group of CYP molecules showing a homology of more than 55% is regarded as a subfamily. When a family contains two or more subfamilies, the subfamilies are denoted in alphabetical order (for example, CYP2A, CYP2B, and CYP2C). Plural CYP molecules contained in a subfamily are denoted by placing an additional Arabic numeral suffix (for example, CYP1A1). At present, Families 1 to 4 are known as drug-metabolism-type CYPs in mammals (non-patent reference 1).

As preferred conditions of dogs used as laboratory large animals, there may be mentioned, for example, (1) homogeneity in form, physiological response, or the like, (2) no genetical lack, and (3) clear birth records (such as parentage or date of birth). The most preferable variety meeting the above conditions is a beagle (non-patent reference 2). Therefore, a beagle is an animal variety widely used in a large animal test for safety and toxicity or pharmacokinetics when compounds are screened at the search stage. In this connection, canine CYPs contributing to a drug metabolizing mechanism in a beagle are gradually becoming clear. Some canine CYP families are identified by various cloning techniques. Full or partial sequences encoding CYP1A1 and CYP1A2 (non-patent reference 3), CYP2B11 (non-patent reference 4), CYP2C21 and CYP2C41 (non-patent reference 3 and non-patent reference 5), CYP2D15 (non-patent reference 6), CYP2E1 (non-patent reference 7), and CYP3A12 and CYP3A26 (non-patent reference 8 and non-patent reference 9) have been cloned. With respect to almost all of the CYPs described above, the full sequences containing an open reading frame (hereinafter referred to as ORF) have been determined, but the sequence encoding CYP1A2 has been only partially determined. A human CYP1 family includes two subfamilies A and B, which are induced by polycyclic aromatic hydrocarbons (such as 3-methylcholanthrene) or 2,3,7,8-tetrachlorodibenzo-p-dioxin (TCDD, dioxin). The drug metabolizing mechanism in the CYP1 family is best maintained among CYPs, and thus substrate specificity in humans is very similar to that of laboratory animals. Oxidation of carcinogenic polycyclic aromatic hydrocarbons or mycotoxins, or hydroxylation of nitrogen atom(s) in aromatic amines or heterocyclic amines are typical reactions, and the CYP1 family is closely associated with a metabolic activation of a carcinogen (non-patent reference 10).

In a beagle, it has been confirmed that CYP1A1 is slightly expressed in lungs, but not expressed in the liver. CYP1A2 is expressed only in the liver, and accounts for approximately 4% of all CYPs expressed in the liver (non-patent reference 3 and non-patent reference 11).

An individual difference in drug responsivity is associated with that in a drug metabolizing ability. Until now, a difference in a drug metabolizing ability was found from a difference in internal dynamics. Tolbutamide, debrisoquine, and sparteine are typically known. It has been clarified that such a difference in internal drug dynamics is due to a difference in an activity of a metabolizing enzyme caused by single nucleotide polymorphism(s) [SNP(s)] in a CYP gene which metabolizes the drug. More particularly, when one or more bases among four kinds of bases contained in DNA are substituted, substitution of amino acid(s) in an enzyme protein, introduction of a stop codon into a DNA sequence, or a flame shift will occur. The substitution of amino acid(s) may sometimes reduce an enzyme activity, and the introduction of a stop codon and a flame shift may sometimes generate an immature protein. Therefore, drugs in which a remarkable individual difference in internal dynamics caused by SNP(s) in a drug metabolizing enzyme is exhibited, are known (non-patent reference 12).

As to SNPs in a human CYP1A2 gene, it was reported that an amount of CYP1A2 expressed was lowered by −3858G>A SNP (mutation CYP1A2*1C) and −164C>A SNP (mutation CYP1A2*1F) located in the upstream region of the gene. However, it was reported, as to −164C>A SNP, that an amount of CYP1A2 expressed was increased by an environmental factor, i.e., smoking, in comparison with genetic factors. Functions of other SNPs in the human CYP1A2 gene are not identified (non-patent reference 13, non-patent reference 14, and non-patent reference 15).

SNPs are most widely examined in CYPs, but new findings can be obtained from enzymes other than CYPs, or drug transporters. Thiopurine S-methyltransferase (hereinafter referred to as TPMT) is an enzyme which catalyzes methylation of some thiopurine drugs. TPMT is mainly located in the liver, but also is located in erythrocytes, and thus erythrocytes are used to analyze phenotypes in humans. When a TPMT activity in erythrocytes is used as an index, activities in whites exhibited a triphasic profile. A group exhibiting a high activity accounted for 88.6%, a group exhibiting a middle activity accounted for 11.1%, and a group exhibiting a low activity accounted for 0.3%. Evans et al. analyzed a TMPT gene in a leukemia patient with acute pancytopenia by 6-mercaptopurine, and revealed that the gene had three point mutations (TPMT*2, TPMT*3A, and TPMT*3C) with amino acid substitutions which caused the disappearance of the enzyme activity (non-patent reference 16). Salavaggione et al. examined a polymorphism in canine TPMT. A phenotype analysis revealed the same individual differences as those in humans, but no significant SNPs in the canine TPMT were found by a gene diagnosis (non-patent reference 17).

Further, some SNPs in a human MDR1 (multi drug resistance) gene encoding a drug transporter, P-glycoprotein (hereinafter referred to as P-gp) were reported. Hoffineyer et al. reported that Caucasian were analyzed, to find that a gene mutation from C to T at position 3435 of exon 26 in the MDR1 gene encoding P-gp reduced an amount of MDR1 expressed in the digestive tract and that a concentration of digoxin was increased in plasma after oral administration (non-patent reference 18). Mealey et al. revealed that differences of sensitivity to a macrolide antibiotic, ivermectin in a Collies central nervous system were due to immature P-gp generated by a frame shift mutation in the mdr1 gene (non-patent reference 19).

As to canine SNPs associated with drug metabolizing enzymes, Paulson et al. reported that beagles could be divided into an extensive metabolizer (hereinafter referred to as EM) group and a poor metabolizer (hereinafter referred to as PM) group with respect to a metabolic rate of a cyclooxygenase II inhibitor, celecoxib. It is thought that a CYP2D subfamily may contribute to the polymorphism, but the details are unknown (non-patent reference 20).

Miyashita et al. revealed that there are two groups of beagles having different patterns of metabolites from a phosphodiesterase IV inhibitor, 4-cyclohexyl-1-ethyl-7-methylpyrido[2,3-d]pyrimidin-2(1H)-one in plasma (non-patent reference 21). Azuma et al. reported that beagles exhibited individual differences in a concentration of metabolites from an α7-nicotine acetylcholine receptor agonist, GTS-21 in plasma, and suggested that differences in an amount of CYP1A expressed might contribute to the individual differences (non-patent reference 22).

Similarly, Mise et al. reported that differences in an amount of CYP1A expressed in beagles caused individual differences in a concentration of an anti-benzodiazepine antagonist, AC-3933 in plasma (non-patent reference 23).

However, SNPs in canine CYPs which can clarify individual differences in a phenotype analysis of a drug metabolizing ability in beagles are not identified in a gene diagnosis.

(non-patent reference 1) Ryuich Kato and Tetsuya Kamataki ed., "YAKUBUTUTAISHAGAKU -IRYOUY-AKUGAKU/DOKUSEIGAKU NOKISOTOSHITE-", 2nd ed., TOKYOKAGAKUDOUZIN, Oct. 2000, p. 9-19

(non-patent reference 2) Hiroshi Otokawa, "INUNOSEIBU-TUGAKU", 1St ed., ASAKURASYOTEN, Sep. 1969, p. 179-187

(non-patent reference 3) "Molecular pharmacology", U.S.A., 1990, Vol. 38, p. 644-651

(non-patent reference 4) "Archives of biochemistry and biophysics", U.S.A., 1990, Vol. 281, p. 106-115

(non-patent reference 5) "Drug metabolism and disposition", U.S.A., 1998, Vol. 26, p. 278-283

(non-patent reference 6) "Archives of biochemistry and biophysics", U.S.A., 1995, Vol. 319, p. 372-382

(non-patent reference 7) "Drug metabolism and disposition", U.S.A., 2000, Vol. 28, p. 98 1-986

(non-patent reference 8) "Biochimica et biophysica acta", U.S.A., 1991, Vol. 1088, p. 319-322

(non-patent reference 9) "The journal of pharmacology and experimental therapeutics", U.S.A., 1997, Vol. 283, p. 1425-1432

(non-patent reference 10) Ryuich Kato and Tetsuya Kamataki ed., "YAKUBUTUTAISHAGAKU -IRYOUY-AKUGAKU/DOKUSEIGAKU NOKISOTOSHITE-", 2nd ed., TOKYOKAGAKUDOUZIN, Oct. 2000, p.19-20

(non-patent reference 11) "Xenobiotica", United Kingdom, 1996, Vol. 26, p. 755-763

(non-patent reference 12) Warner Kalow, Urs Meyer, and Rachel Tyndale ed., Tomohisa Ishikawa trans-ed., "PHARMACOGENOMICS -21 SEIKTNOSOUYAKU-TOKONOIRYOU-", 1st ed., TECHNOMICS, Dec. 2002, p. 29-43

(non-patent reference 13) "The Journal of Biochemistry", Japan, 1999, Vol. 125, p. 803-808

(non-patent reference 14) "British journal of clinical pharmacology", United Kingdom, 1999, Vol. 47, p. 445-449

(non-patent reference 15) "Pharmacogenetics", U.S.A., 1999, Vol. 9, p. 367-375

(non-patent reference 16) Ryuich Kato and Tetsuya Kamataki ed., "YAKUBUTUTAISHAGAKU -IRYOUY-AKUGAKU/DOKUSEIGAKU NOKISOTOSHITE-", 2nd ed., TOKYOKAGAKUDOUZIN, Oct. 2000, p. 141-155

(non-patent reference 17) "Pharmacogenetics", U.S.A., 2002, Vol. 12, p. 713-724

(non-patent reference 18) "Proceedings of the National Academy of Sciences of the United States of America", U.S.A., 2000, Vol. 97, p. 3473-3478

(non-patent reference 19) "Pharmacogenetics", U.S.A., 2001, Vol. 11, p. 722-733

(non-patent reference 20) "Drug metabolism and disposition", U.S.A., 1999, Vol. 27, p. 1133-1142

(non-patent reference 21) "The 17th Annual Meeting of the Japanese Society for the Study of Xenobiotics, poster session", Japan, 2002, 2OPE-46

(non-patent reference 22) "Drug metabolism and pharmacokinetics", Japan, 2002, p. 75-82

(non-patent reference 23) "Drug metabolism and disposition", U.S.A., 2004, Vol. 32, p. 240-245

DISCLOSURE OF INVENTION

PROBLEMS TO BE SOLVED BY THE INVENTION

Because a pharmacological effect test or a toxicity test for compounds as candidates for medicaments is carried out using dogs exhibiting large individual differences in a metabolizing ability which affects internal dynamics on which the pharmacological effect or toxicity of each compound depends, there are considerable individual differences in the pharmacological effect test or toxicity test, and thus the resulting data vary widely.

Objects of the present invention are to provide a convenient method capable of carrying out a rapid gene diagnosis of a CYP1A2 gene of dogs (particularly beagles) used in a pharmacological effect test or a toxicity test prior to the test, and further capable of dividing the dogs into a group having a normal metabolic ability (an EM group) and a group having a low metabolic ability (a PM group); and thereby to make it possible to carry out a pharmacological effect test or a toxicity test by genetically homogeneous individuals and evaluate a pharmacological effect or toxicity accurately.

MEANS FOR SOLVING THE PROBLEMS

The present inventors have conducted intensive studies and, as a result, selected 4-cyclohexyl-1-ethyl-7-methylpyrido[2,3-D]pyrimidin-2(1H)-one as a test compound which was a substrate specific to CYP1A2; determined SNPs in a canine CYP1A2 gene which determined Types EM and PM of the test compound; and found that a stop codon was generated by a base substitution within the ORF of the CYP1A2 gene in Type PM. Further, the present inventors established convenient methods (an ASP-PCR method and a direct sequence method) for detecting sequences at the SNP sites from a blood sample; determining sequences of the SNP regions from EM and PM groups (five individuals per group) in which 4-cyclohexyl-1-ethyl-7-methylpyrido[2,3-D]pyrimidin-2(1H)-one was administered; and confirming that a stop codon was generated by a base substitution in all individuals of the PM group, and that all individuals of the EM group had a CYP1A2 gene without such a newly generated stop codon heterogeneously or homogeneously; and thus the present invention was completed.

The present invention relates to:

[1] a method for detecting a canine CYP1A2 genetic polymorphism, characterized by determining a base corresponding to a base at position 1117 of a canine CYP1A2 gene (at position 1179 of the nucleotide sequence of SEQ ID NO: 22),

[2] a method for determining which dog is an extensive metabolizer or a poor metabolizer in the rate of drug metabolism, the method comprising:

preparing a nucleic acid sample from a dog, and determining a base corresponding to a base at position 1117 of a canine CYP1A2 gene (at position 1179 of the nucleotide sequence of SEQ ID NO: 22 or at position 87 of exon 4),

[3] a method for selecting a dog used in a medicament test, comprising determining which dog is an extensive metabolizer or a poor metabolizer in the rate of drug metabolism by the method of [2],

[4] a method for assaying a pharmacological effect and/or toxicity of a test drug, comprising administering a test drug to an extensive metabolizer group or a poor metabolizer group selected by the method of [3],

[5] a single stranded DNA consisting of 15 to 30 nucleotides, which hybridizes to a sense strand or an antisense strand of a canine CYP1A2 gene having the nucleotide sequence of SEQ ID NO: 1 or the nucleotide sequence consisting of nucleotides 63-1601 of SEQ ID NO: 22, or a genetic polymorphism thereof under stringent conditions, and selected from the group consisting of:

(1) a single stranded DNA consisting of 15 to 30 nucleotides, wherein a base corresponding to a base at position 405 of the nucleotide sequence of SEQ ID NO: 1 or at position 1179 of the nucleotide sequence of SEQ ID NO: 22 is contained, and the corresponding base is C;

(2) a single stranded DNA consisting of 15 to 30 nucleotides, wherein a base corresponding to a base at position 405 of the nucleotide sequence of SEQ ID NO: 1 or at position 1179 of the nucleotide sequence of SEQ ID NO: 22 is contained, and the corresponding base is T; and (3) a single stranded DNA consisting of 15 to 30 nucleotides, which is a strand complementary to the single stranded DNA (1) or (2),

[6] the single stranded DNA of [5], consisting of the nucleotide sequence of SEQ ID NO: 14 or 16, and

[7] an agent for diagnosing a polymorphism in metabolic activity of a drug which is a substrate specific to canine CYP1A2, the agent comprising as an active ingredient a reagent for detecting a base corresponding to a base at position 1117 of a canine CYP1A2 gene (at position 1179 of the nucleotide sequence of SEQ ID NO: 22).

EFFECTS OF THE INVENTION

In the present invention, the present inventors found an SNP in which a base corresponding to a base at position 1117 of a canine CYP1A2 gene (i.e., at position 87 of exon 4) is substituted from C to T. According to the SNP, a codon encoding arginine (Arg) at position 373 of CYP1A2 changes to a stop codon. As a result, CYP1A2 is not expressed in a dog having a T/T genotype, and thus it is predicted that concentrations of drugs metabolized by CYP1A2 in plasma may become extremely high in comparison with a dog having a C/C genotype or a C/T genotype. As described in Examples, the prediction has been proved from internal dynamics of a phosphodiesterase IV inhibitor, Compound A. Further, the present inventors established an ASP-PCR method and a direct sequence method, as a method capable of conveniently detecting the SNP. The present inventors carried out a CYP1A2 gene diagnosis of 65 dogs using these methods to reveal an allele frequency.

As clarified in the present invention, the canine CYP1A2 sometimes contains the stop-codon-causing SNP at position 1117 (i.e., at position 87 of exon 4), and approximately 15% of the dogs have the SNP homogeneously. As shown in experiments with Compound A, the SNP is a major factor for individual differences in internal dynamics of drugs metabolized by CYP1A2 in a dog. Pharmacological effects and toxicity of a compound depend on internal dynamics. Therefore, it is considered that when the compound is metabolized by CYP1A2, remarkable individual differences are observed in evaluating pharmacological effects and toxicity thereof. According to the present invention, a CYP1A2 gene diagnosis of dogs used in a pharmacological effect test or a toxicity test can be rapidly carried out prior to the test. As a result, a pharmacological effect test or a toxicity test can be carried out using genetically homogeneous individuals, and a pharmacological effect or toxicity can be evaluated more accurately than conventional methods used prior to the present invention.

BEST MODE FOR CARRYING OUT THE INVENTION

[A] Detection Method and Dog Selection Method of the Present Invention

In the detection of the present invention, a polymorphism in a canine CYP1A2 gene is detecting by determining a base corresponding to a base at position 1117 of the canine CYP1A2 gene (at position 1179 of the nucleotide sequence of SEQ ID NO: 22). The term "a base corresponding to a base at position 1117 of a canine CYP1A2 gene" as used herein means a base corresponding to "a base at position 1179 of the nucleotide sequence of SEQ ID NO: 22" in a canine CYP1A2 gene. As canine CYP1A2 genes, there are various nucleotide sequences, for example, a partial nucleotide sequence of a CYP1A2 gene described in MOLECULAR PHARMACOLOGY, 1990, Vol. 38, p. 644-651; a nucleotide sequence consisting of nucleotides 63-1601 of SEQ ID NO: 22 first determined by the present inventors in the present invention; or nucleotide sequences of allele variants thereof. Therefore, a base corresponding to "a base at position 1179 of the nucleotide sequence of SEQ ID NO: 22" is not particularly limited, so long as it is a base at position 1117 of a canine CYP1A2 gene. Namely, it is not necessary for each flanking sequence at either the 5' or 3' side of the 1117th base to accord exactly with that of SEQ ID NO: 22.

Further, in the detection method of the present invention, a nucleic acid sample is prepared from a dog, and a base corresponding to a base at position 1117 of a canine CYP1A2 gene (i.e., at position 87 of exon 4) is determined, to detect or determine which dog is an extensive metabolizer (EM) or a poor metabolizer (PM) in the rate of drug metabolism. When the base is a C/C genotype or a C/T genotype, it can be judged that the dog is EM. When the base is a T/T genotype, it can be judged that the dog is PM. As the EM, the C/C genotype is preferable.

Furthermore, in the dog selection method of the present invention, a dog used in a medicament test is selected by detecting or determining whether or not a dog is EM or PM by the above detection method of the present invention.

1. Preparation of Sample Containing Canine Nucleic Acid

A nucleic acid sample used in the method of the present invention, preferably a sample containing canine genomic DNA, may be prepared from a material isolated from a dog (particularly a beagle), such as cells other than germ cells, tissues, or organs. As the material, leukocytes or mononuclear cells are preferable, and leukocytes are most preferable. Such materials can be isolated in accordance with conventional methods commonly used in a biochemical test.

For example, leukocytes are used as the material, peripheral blood is taken from a dog such as a beagle, and leukocytes are separated from the peripheral blood in accordance with a conventional method. To the obtained leukocytes, proteinase K and sodium dodecyl sulfate (SDS) are added to digest and denature proteins, and then a phenol/chloroform extraction is carried out to obtain genomic DNA including RNA. The RNA may be removed by RNase, if necessary. The method of extracting genomic DNA is not limited to the phenol/chloroform extraction, and the genomic DNA may be extracted by, for example, a well-known method [for example, Sambrook, J. et al. (1989): "Molecular Cloning: A Laboratory Manual (2nd Ed.)" Cold Spring Harbor Laboratory, NY] or a commercially available DNA extraction kit. Further, cDNA prepared from canine mRNA extracted in accordance with a conventional method may be used in detecting a genetic polymorphism.

2. Detection of Genetic Polymorphism

Next, the obtained sample containing canine nucleic acid is used to diagnose a genotype of the SNP, revealed by the present inventors, in which a base corresponding to a base at position 1117 of a CYP1A2 gene (at position 87 of exon 4) is substituted from C to T. Hereinafter, typical methods for detecting a genomic polymorphism, which may be used in the method of the present invention, will be explained.

(1) RFLP (Restriction Fragment Length Polymorphism) Method

When a genomic polymorphic site is located in a restriction enzyme recognition site, the genomic polymorphism can be detected on the basis of a difference in length of each DNA fragment generated by digestion with the restriction enzyme. The detection may be carried out, for example, (a) by digesting DNA with a restriction enzyme, and carrying out Southern blotting, or (b) by amplifying a DNA fragment containing a polymorphic site by PCR, digesting the PCR product with a restriction enzyme, and analyzing the sizes of digested DNA fragments by electrophoresis.

As a probe used in the above method (a), a DNA fragment (labeled with, for example, an isotope, biotin, or a fluorescent dye) corresponding to a sequence containing the polymorphic site of interest and the 5' and 3' flanking sequences (approximately 0.5 to 2 kb) is preferable. As a PCR primer used in the above method (b), an oligonucleotide consisting of 15 to 30 nucleotides for amplifying an approximately 0.05 to 4 kb of DNA fragment containing the polymorphic site is preferable.

(2) PCR-SSCP (Single Strand Conformational Polymorphism) Method

The PCR-SSCP method is a method in which a DNA fragment containing a genetic polymorphic site is amplified by PCR, and the PCR product is thermally-denatured and applied to electrophoresis to separate single stranded DNAs having different conformations (Biotechniques, 1994, Vol. 16, p. 296-297; and Biotechniques, 1996, Vol. 21, p. 510-514). An electrophoretic migration of a single stranded DNA depends on the presence or absence of genetic polymorphisms, and thus a polymorphic typing can be carried out by analyzing the electrophoretic pattern. As a standard for typing, it is preferable to use a DNA sample in which a nucleotide sequence containing the polymorphic site is previously determined, as a template DNA of PCR, together with a test sample. As a primer for PCR amplification, an oligonucleotide consisting of 15 to 30 nucleotides for amplifying an approximately 50 to 500 bp of DNA fragment containing the polymorphic site is preferable.

(3) ASO (Allele Specific Oligonucleotide) Hybridization Method

The ASO hybridization method is a method in which a DNA fragment containing a genetic polymorphic site is dot-blotted on a support (such as a nylon filter), a hybridization with probes corresponding to each genetic polymorphism is carried out, and a washing treatment in accordance with a Tm (melting temperature) value of each probe is carried out to detect a polymorphism (i.e., when a probe is mismatched to the corresponding polymorphic site, the hybridized probe is removed from the support by the washing treatment) (Clinica chimica acta; international journal of clinical chemistry, 1990, Vol. 189, p. 153-157). As the probe, a synthetic oligonucleotide consisting of approximately 15 to 25 nucleotides is preferable. To obtain a signal derived from the probe, it is necessary to label the probe with, for example, an isotope, biotin, or a fluorescent dye.

(4) Direct Sequence Method

The direct sequence method is a method in which a DNA fragment containing a genetic polymorphic site is amplified by PCR, and the nucleotide sequence of the amplified DNA is directly analyzed by a dideoxy method (Biotechniques, 1991, Vol. 11, p. 246-249). As a PCR primer used in this method, an oligonucleotide consisting of 15 to 30 nucleotides for amplifying an approximately 0.05 to 4 kb of DNA fragment containing the polymorphic site is preferable. As a sequence primer, an oligonucleotide consisting of 15 to 30 nucleotides corresponding to a sequence located at an approximately 50 to 300 nt 5' upstream from the polymorphic site is preferable.

(5) ASP-PCR (Allele Specific Primer-PCR) Method

In PCR, a primer and a template DNA are annealed, and then a complementary DNA is synthesized from the 5' terminus to the 3' terminus by DNA polymerase. When a base at the 3' terminus of the primer is mismatched to the template, the efficiency of PCR is reduced and no PCR product may be detected by electrophoresis. The ASP-PCR method is a method in which PCR is carried out using a primer, the 3' terminal base of which is designed to be complementary to a mutated base to be detected, to detect a genetic polymorphism on the basis of the presence or absence of the amplified product (Nucleic acids research, 1991, Vol. 19, p. 3561-3567; and Nucleic acids research, 1992, Vol. 20, p. 4831-4837). As a pair of PCR primers used in this method, one primer is an oligonucleotide (preferably 15 to 30 nt), the 3' terminus of which is designed to correspond to the polymorphic site, and the other is preferably an oligonucleotide consisting of 15 to 30 nucleotides corresponding to a sequence at a distance of an approximately 0.05 to 2 kb from the polymorphic site.

(6) Denaturing Gradient Gel Electrophoresis (DGGE) Method

The DGGE method is a method of detecting a genetic polymorphism on the basis of the fact that a heteroduplex having a mismatch(es) in a DNA fragment is easily disassociated, compared with a homoduplex (Biotechniques, 1999, Vol. 27, p. 1016-1018). As the disassociation of a heteroduplex progresses, an electophoretic migration of a heteroduplex in gel becomes lower. When a density gradient of urea and formamide is previously formed in a polyacrylamide gel used, a difference between the migrations of a heteroduplex and a homoduplex is emphasized, and thus the presence of a double stranded DNA having a mismatch(es), i.e., the presence of mutation(s), can be detected. As a PCR primer used in this method, an oligonucleotide consisting of 15 to 30 nucleotides for amplifying an approximately 0.05 to 0.5 kb of DNA fragment containing the polymorphic site is preferable.

(7) RNase A Digestion Method

RNase A (ribonuclease) does not digest a double stranded RNA or a RNA/DNA complex, but digests only a single stranded RNA. When a DNA fragment having a polymorphic site is amplified by PCR, the PCR product is denatured to be single stranded DNA fragments, an isotope-labeled RNA probe is hybridized to the denatured DNA fragments, the mixture is treated with RNase A, and the reaction mixture is applied to electrophoresis; the RNA probe which hybridizes to a DNA fragment having a mutated base is digested at the mismatched site, and thus may be detected as two bands (DNA and cell biology, 1995, Vol. 14, p. 87-94). As an RNA probe used in this method, an oligonucleotide consisting of generally 15 to 30 nucleotides and containing the polymorphic site is preferable.

(8) Chemical Cleavage Method

After a DNA fragment containing a polymorphic site is amplified by PCR, "C (cytosine)" and "T (thymine)" at a mismatched site in a double stranded DNA are modified with hydroxylamine and osmium tetroxide, respectively, and then the modified DNA fragment is treated with piperidine to cleave a saccharide portion thereof. A labeled probe is used to form a double strand, the double strand is treated as above, and the reaction mixture is applied to electrophoresis. When a shortened probe is detected, the result indicates the presence of a mutation (Biotechniques, 1996, Vol. 21, p. 216-218). As a PCR primer used in this method, an oligonucleotide consisting of 15 to 30 nucleotides for amplifying an approximately 0.05 to 4 kb of DNA fragment containing the polymorphic site is preferable.

(9) DOL (Dye-Labeled Oligonucleotide Ligation) Method

The DOL method is a method in which a DNA fragment containing a genetic polymorphism is amplified by PCR, and a fluorescence-labeled dye primer containing at least a base proximate to the polymorphic site, and a dye terminator labeled with a fluorescent dye specific to each allele, are ligated with a heat resistant DNA ligase (Genome research, 1998, Vol. 8, p. 549-556). As a PCR primer used in this method, an oligonucleotide consisting of 15 to 30 nucleotides for amplifying an approximately 0.05 to 2 kb of DNA fragment containing the polymorphic site is preferable.

(10) TaqMan PCR Method

In the TaqMan PCR method, fluorescence-labeled and allele-specific oligonucleotides (TaqMan probe) and TaqDNA polymerase are used to carry out PCR (Genetic analysis: biomolecular engineering, 1999, Vol. 14, p. 143-149; and Journal of clinical microbiology, 1996, Vol. 34, p. 2933-2936). As a PCR primer used in this method, an oligonucleotide consisting of 15 to 30 nucleotides for amplifying an approximately 0.05 to 2 kb of DNA fragment containing the polymorphic site is preferable. As the TaqMan probe, the 5' and 3' termini of which are labeled with a fluorescent reporter dye and a quencher, respectively, an oligonucleotide consisting of approximately 15 to 30 nucleotides and containing the polymorphic site is preferable. Base mutations in a wild type and variants can be detected by using such probes.

(11) Invader Method

In the invader method, two non-fluorescence-labeled oligonucleotides and a fluorescence-labeled oligonucleotide are used. One (hereinafter referred to as "allele probe") of the non-fluorescence-labeled oligonucleotides is composed of a "flap" sequence [i.e., a sequence irrelevant to a genomic sequence (hereinafter referred to as "template") containing a polymorphic site to be detected] at the 5' terminal side of the allele probe, and a complementary sequence specific to a sequence at the 5' terminal side of the polymorphic site in the template, at the 3' terminal side of the allele probe. That is, the 5' terminus of the above complementary sequence in the allele probe corresponds to the polymorphic site in the template. The other non-fluorescence-labeled oligonucleotide (hereinafter referred to as "invader probe") has a complementary sequence specific to a sequence at the 3' terminal side of the polymorphic site in the template. The 3' terminus of the invader probe corresponds to the polymorphic site in the template, but is not limited to a base complementary to a base at the polymorphic site in the template. The fluorescence-labeled oligonucleotide [hereinafter referred to as "FRET (fluorescence resonance energy transfer) probe"] is composed of a complementary sequence to the flap, at the 3' terminal side of the FRET probe, and a palindromic sequence which forms a double strand, at the 5' terminal side of the FRET probe. The FRET probe is labeled with a fluorescent dye close to the 5' terminus thereof, and a quencher, which can counteract the fluorescence, is bound to the 5' terminus of the FRET probe.

First, the allele probe and the invader probe are hybridized to the template. When the allele probe is complementary to the template at the polymorphic site, the template, the 5' terminus of the allele probe, and the 3' terminus of the invader probe form a special structure at the polymorphic site. An enzyme (hereinafter referred to as cleavase) which specifically recognizes the special structure and exhibits an endonuclease activity remove the flap portion from the allele probe. The released flap is hybridized to the 3' terminal side of the FRET probe. The flap and the FRET probe form, at the 5' terminus to which a quencher of the FRET probe is bound, a structure specifically recognized by the cleavase, and thus, the 5' terminal nucleotide with the quencher is removed from the FRET probe by the cleavase. As a result, the fluorescent dye on the FRET probe emits fluorescence.

In contrast, when the allele probe is not complementary and is mismatched to the template at the polymorphic site, the structure specifically recognized by the cleavase is not formed, and thus, the flap is not removed from the allele probe. In this case, the flap which is not removed and is maintained in the allele probe may be hybridized to the 3' terminal side of the FRET probe, but an efficiency of removing the 5' terminal nucleotide with the quencher from the FRET probe by the cleavase is low, in comparison with the case that the flap removed from the allele probe is hybridized thereto, and thus, the strength of fluorescence emitted from the FRET probe is low. According to the principle described above, a polymorphism can be detected (Science, 1993, Vol. 5109, 778-783; The journal of biological chemistry, 1999, Vol. 30, p. 21387-21394; and Nature biotechnology, 1999, Vol. 17, p. 292-296).

(12) MALDI-TOF/MS (Matrix Assisted Laser Desorption-Time of Flight/Mass Spectrometry) Method The MALDI-TOF/MS method is a typing method by synthesizing single stranded oligonucleotides comprising a different nucleotide sequence corresponding to each allele of a genetic polymorphism of interest, measuring each mass thereof, and detecting differences by a mass spectrometer (Genome research, 1997, Vol. 7, p. 378-388; European journal of clinical chemistry and clinical biochemistry: journal of the forum of European clinical chemistry societies, 1997, Vol. 35, p. 545-548). In the MALDI-TOF/MS method, a DNA fragment containing a polymorphic site is amplified by PCR, a primer adjacent to the polymorphic site is used to carry out an elongation reaction, and the resulting product specific to each allele is analyzed on the basis of mass spectrum. As a PCR primer used in this method, an oligonucleotide consisting of 15 to 30 nucleotides for amplifying an approximately 0.05 to 0.5 kb of DNA fragment containing the polymorphic site is preferable. As a primer for detecting a polymorphism, an oligonucleotide consisting of 15 to 30 nucleotides adjacent to the polymorphic site is preferable.

(13) TDI (Template-Directed Dye-Terminator Incorporation) Method

The TDI method is a method in which a DNA fragment containing a genetic polymorphism is amplified by PCR, and a primer designed to proximate to the polymorphic site is used to incorporate a dideoxynucleotide labeled with a different fluorescent dye corresponding to each allele into the polymorphic site, by a primer elongation reaction (Proceedings of the National Academy of Sciences of the United States of America, 1997, Vol. 94, p. 10756-10761). The primer elongation product is analyzed, for example, by a DNA sequencer (ABI PRISM 377, Applied Biosystems). As a PCR primer used in this method, an oligonucleotide consisting of 15 to 30 nucleotides for amplifying an approximately 0.05 to 1 kb of DNA fragment containing the polymorphic site is preferable.

(14) Molecular Beacons Method

The molecular beacon is an oligonucleotide having a quencher and a fluorophore at both termini, respectively. It is preferable that the molecular beacon has a stem loop structure composed of a stem portion of 5 to 7 nucleotides and a loop structure of 15 to 30 nucleotides. The fluorophore does not emit fluorescence by an action of the quencher, even if an excitation light is irradiated. When a nucleotide sequence in the loop structure is hybridized to a target DNA having a sequence homologous to the nucleotide sequence in the loop structure, the distance between the fluorophore and the quencher is increased, and thus the fluorophore emits fluorescence when irradiated with an excitation light (Nature biotechnology, 1998, Vol. 1, p. 49-53; and IDENSHIIGAKU, 2000, Vol. 4, p. 46-48). The nucleotide sequence of the step portion of the molecular beacon is not complementary to that of a target DNA. As to a Tm value of the stem structure of the molecular beacon, when the molecular beacon is added to a reaction mixture for amplifying a target region by PCR and fluorescence is measured at an annealing temperature of PCR by irradiating an excitation light, fluorescence is emitted if the molecular beacon has an absolutely homologous sequence to the target gene and is hybridized thereto. In contrast, if the molecular beacon is mismatched to the target gene, the molecular beacon is not hybridized to the target, and thus does not emit fluorescence. A genetic polymorphism can be detected by this method.

(15) Dynamic Allele-Specific Hybridization (DASH) Method

In the DASH method, a primer in which the terminus is biotinylated is used when a target DNA (60 to 90 bp) is amplified from a genomic DNA by PCR (Nature biotechnology, 1998, Vol. 1, p. 87-88; and IDENSHIIGAKU, 2000, Vol. 4, p. 47-48). After the PCR, a strand containing a biotinylated primer binds to a microtiter well coated with streptavidin. In contrast, a strand containing an unmodified primer cannot bind to the microtiter well, and is easily removed by a rinse treatment with an alkaline solution. Then, a probe DNA (preferably 15 to 21 nt) is hybridized to the strand containing the biotinylated primer. In this hybridization step, a fluorescent substance (such as syber green I dye) which specifically binds to a double stranded DNA and emits fluorescence is incorporated into the hybrid DNA. After the hybridization, the hybrid DNA is denatured while measuring the strength of the fluorescence. If the target DNA is not absolutely complementary and is mismatched to the probe DNA, a temperature at which the hybrid DNA is denatured and fluorescence is not emitted is low, in comparison with the case that the target DNA is absolutely complementary to the probe DNA. A genetic polymorphism can be detected by observing the difference in the above temperature.

(16) Padlock Probe Method

The Padlock probe method was developed by Lizardi et al. (Nature genetics, 1998, Vol. 3, p. 225-232; and IDENSHIIGAKU, 2000, Vol. 4, p. 50-51). A probe is designed to be circularized by hybridizing to a single stranded target DNA. The probe is hybridized to the target DNA, circularized DNA is ligated with DNA ligase to become a circular DNA, and an alkaline phosphatase [such as Calf intestinal alkaline phosphatase (CIAP)] treatment is carried out to remove a phosphate group. If there is a mismatch at the terminus and the DNA is not circularized, the phosphate group is removed and thus the DNA cannot become a circular DNA. Next, Primer (1) is designed with respect to the circular DNA, and a replication reaction is carried out with DNA polymerase to obtain replicon multimers. Primer (2) is designed with respect to the replicon, and double stranded DNAs are amplified by DNA polymerase using a mixture of Primers (1) and (2). In this connection, Primer (1) is designed on the basis of a portion not complementary to the target DNA. Primer (2) is designed on the basis of a sequence (containing a genetic polymorphism at the 3' terminus) complementary to the terminal portion (target DNA) of circularized probe (padlock probe). A primer in which the 3' terminal base is substituted is used for detecting a polymorphism. With respect to the padlock probe, an amplification reaction is carried out by a hyperbranched rolling-circle amplification (HRCA) method, which is a modification of a rolling circle-reaction (RCA) method. The reaction mixture is treated with a restriction enzyme which recognizes a restriction enzyme recognition site located in the padlock probe, and the presence or absence of bands is analyzed by electrophoresis.

(17) UCAN Method

In the UCAN method (see http://www.takara.co.jp), the 3' terminal DNA in a DNA-RNA-DNA primer (DRD primer) in which RNA is interposed between DNAs is chemically modified so as not to replicate a template DNA by DNA polymerase. The DRD primer designed to hybridize to a polymorphic site having a possibility of one-base-mutation via the RNA portion is hybridized to a template DNA. If the DRD primer is absolutely matched to the template, the hybridized RNA portion of the DRD primer is digested by RNase H. Because the digestion generates a new 3' terminus, an elongation reaction with DNA polymerase progresses to amplify the template DNA. In contrast, if the DRD primer is not matched to the template DNA at the site (i.e., when an SNP is present), RNase H does not digest the DRD primer, and thus the DNA amplification does not occur. A genetic polymorphism can be detected by detecting the presence or absence of the gene amplification.

(18) DNA Chip or DNA Microarray

In a DNA chip or DNA microarray, various DNA probes containing various polymorphic sites are immobilized on a glass base, and labeled nucleic acid samples are hybridized to the probes to detect the presence or absence of polymorphisms by a fluorescent signal. Generally, an apparatus in which DNAs are synthesized on the glass base is called a DNA chip (oligo DNA chip), and an apparatus in which cDNAs are placed on the glass base is called a DNA microarray. As a probe immobilized or synthesized on the base, an oligonucleotide consisting of approximately 20 nucleotides and containing a polymorphic site is preferable for an oligo DNA chip, and a double stranded DNA consisting of approximately 100 to 1500 nucleotides for a cDNA microarray.

(19) ECA (Electrochemical Array) Method

The ECA method is a gene typing method based on the electrochemical properties of an intercalator which binds to a double stranded DNA. A region containing a polymorphism is amplified by PCR, the PCR product is hybridized to each allele-complementary probe immobilized on a base, and an intercalator is reacted. In this case, an amount of intercalator bound to each probe depends on an absolute complementation or an imperfect complementation. Because an intercalator used in the ECA method contains ferrocene having electrochemical properties, electrical signals are different in proportion to amounts of intercalator bound. The ECA method is a method for detecting a genetic polymorphism on the basis of the difference in the signals (Analytical chemistry, 2000, Vol. 72, p. 1334-1341).

The methods described above, but not limited to, are typical methods of detecting a genetic polymorphism which can be used in the present invention. In the present invention, other methods of detecting a genetic polymorphism may be used, and further, such methods may be used singly or in a combination thereof. In Examples described below, embodiments of the present invention using the ASP-PCR method or the direct sequence method will be described.

[B] Assay Method of the Present Invention

In the assay method of the present invention, by which whether a dog is EM or PM in the rate of drug metabolism is determined by the detection method of the present invention, a dog used in a medicament test is selected, a test drug is administered to an EM group or a PM group, and a pharmacological effect and/or toxicity of the test drug is assayed. It is preferable that the EM group (more preferably a dog having a C/C genotype) is used.

A method for assaying a pharmacological effect of a test drug may be appropriately selected in accordance with an indication of the test drug.

As to a method for assaying a toxicity of a test drug, a conventional method may be used, and there may be mentioned, for example, single oral dose toxicity study in beagles, 2-week oral toxicity study in beagles, single dose intravenous toxicity study in beagles, 1-week intravenous toxicity study in beagles, 4-week intravenous toxicity study in beagles, 1-week intravenous infusion toxicity study in beagles, 4-week intravenous infusion toxicity study in beagles, single intravenous dose increment toxicity study in beagles, 2-week intravenous infusion toxicity study in beagles, 4-week oral toxicity study in beagles, 13-week oral toxicity study in beagles, or 52-week oral toxicity study in beagles (Mahin Maines et al., Current protocols in toxicology volume 1, 2, John Wiley & Sons. Inc., 2001, p. 1.0.1-16.6.5; and Yasuhiko Shirasu and Toyoaki Toyama, ed., DOKUSEISIKEN handbook, SCIENCE FORUM, May 1980, p. 81-282).

In the assay method of the present invention, the step of selecting a dog and the step of assaying a pharmacological effect and/or toxicity of a test drug can be carried out separately. The present invention includes a method comprising the steps of preparing a dog found to be in an EM group or a PM group by the method of the present invention, and assaying a pharmacological effect and/or toxicity of a test drug using only one of the EM group or the PM group.

[C] Single Stranded DNA and Agent for Diagnosing a Polymorphism in Metabolic Activity The single stranded DNA of the present invention hybridizes to a sense strand or an antisense strand of a canine CYP1A2 gene having the nucleotide sequence of SEQ ID NO: 1 or the nucleotide sequence consisting of nucleotides 63-1601 of SEQ ID NO: 22, or a genetic polymorphism thereof under stringent conditions, and is a single stranded DNA composed of 15 to 30 nucleotides, selected from the group of:

(1) a single stranded DNA consisting of 15 to 30 nucleotides, wherein a base corresponding to a base at position 405 of the nucleotide sequence of SEQ ID NO: 1 or at position 1179 of the nucleotide sequence of SEQ ID NO: 22 is contained, and the corresponding base is C [preferably a single stranded DNA consisting of the nucleotide sequence of SEQ ID NO: 14 (i.e., primer S07wild used in Example 4)];

(2) a single stranded DNA consisting of 15 to 30 nucleotides, wherein a base corresponding to a base at position 405 of the nucleotide sequence of SEQ ID NO: 1 or at position 1179 of the nucleotide sequence of SEQ ID NO: 22 is contained, and the corresponding base is T [preferably a single stranded DNA consisting of the nucleotide sequence of SEQ ID NO: 16 (i.e., primer S07mutant used in Example 4)]; and (3) a single stranded DNA consisting of 15 to 30 nucleotides, which is a strand complementary to the single stranded DNA (1) or (2).

The term "a base corresponding to a base at position 405 of the nucleotide sequence of SEQ ID NO: 1 or at position 1179 of the nucleotide sequence of SEQ ID NO: 22" is not particularly limited, so long as it is a base at position 405 of the nucleotide sequence of SEQ ID NO: 1 or at position 1179 of the nucleotide sequence of SEQ ID NO: 22. Namely, it is not necessary for each flanking sequence at either the 5' or 3' side of the base to accord exactly with that of SEQ ID NO: 1 or 22.

The term "stringent conditions" as used herein is not particularly limited, but preferably denotes conditions of the reaction system described in Example 4 [a PCR buffer for KOD (final concentration: 1×), dNTP mix (final concentration: each 0.2 mmol/L), magnesium sulfate (final concentration: 1 mmol/L), a PCR primer set (final concentration: each 0.3 mmol/L), and KOD-plus- (final concentration: 0.02

Unit)] and the PCR reaction condition described in Example 4 (performing a reaction at 94° C. for 2 minutes, repeating a cycle consisting of reactions at 94° C. for 15 seconds, at 56° C. for 30 seconds, and at 68° C. for 30 seconds 35 times, and performing a reaction at 68° C. for 1.5 minutes).

The single stranded DNA of the present invention may be used in detecting a genetic polymorphism in a base corresponding to a base at position 1117 of a canine CYP1A2 gene (i.e., at position 87 of exon 4), i.e., a base corresponding to a base at position 1179 of the nucleotide sequence of SEQ ID NO: 22 or at position 405 of the nucleotide sequence of SEQ ID NO: 1, more particularly, in determining whether the base of interest is C or T.

As the single stranded DNA of the present invention, a DNA consisting of the nucleotide sequence of SEQ ID NO: 14 or 16 is most preferable.

The present invention includes an agent for diagnosing a polymorphism in metabolic activity of a drug which is a substrate specific to canine CYP1A2, comprising as an active ingredient a reagent for detecting a base corresponding to a base at position 1117 of a canine CYP1A2 gene. The detecting reagent includes, for example, the single stranded DNA of the present invention.

EXAMPLES

The present invention now will be further illustrated by, but is by no means limited to, the following Examples.

Example 1

Determination of SNPs in Beagle CYP1A2 Gene

In this example, total RNA isolated from a beagle liver was used as a template, a partial nucleotide sequence of beagle CYP1A2 cDNA was determined by a RT-PCR (Reverse transcription-polymerase chain reaction) method, and SNPs in a beagle CYP1A2 gene were determined, in accordance with the following procedures.

A beagle A (type EM) and a beagle B (type PM), previously classified by a preliminary test (see Example 7), were anesthetized and sacrificed by intravenously administering 50 mg/mL/kg of pentobarbital (two subjects in total), and the liver of each was dissected and immediately frozen. An RNeasy Mini kit (QIAGEN) was used to obtain each total RNA from the frozen livers in accordance with a protocol attached to the kit.

From the obtained total RNA, 500 ng of total RNA was used as a template to synthesis cDNA from RNA by a reverse transcriptase. The reaction was carried out using an RNA LA PCR kit Ver.1.1. (Takara Shuzo). The conditions in the reverse transcription reaction are shown in Table 1. The volume "×µL" of the "RNase-free sterile water" in Table 1 means that the total volume of the reaction system was adjusted to 40.0 µL by adding an appropriate volume of RNase-free sterile water.

TABLE 1

| | Reaction system: | |
|---|---|---|
| 25 mmol/L | magnesium chloride | 8.0 µL |
| 10× | RNA PCR buffer | 4.0 µL |
| each 10 mmol/L | dNTP mix | 4.0 µL |
| 40 U/µL | RNase inhibitor | 1.0 µL |
| 5 U/µL | AMV reverse transcriptase | 2.0 µL |
| 2.5 µmol/L | random primer (Random 9mer) | 2.0 µL |
| | RNase-free sterile water | x µL |
| | total RNA | 500.0 ng |
| Total | | 40.0 µL |

[Reverse transcription reaction conditions: at 30° C. for 10 minutes, at 55° C. for 20 minutes, at 95° C. for 5 minutes, and at 5° C. for 5 minutes (1 cycle)]

The single stranded cDNA synthesized in the above reverse transcription reaction was used as a template to carry out PCR by DNA polymerase KOD-plus- (Toyobo). As PCR primer sets for recognizing a partial nucleotide sequence of canine CYP1A2 cDNA, a set of primer S01 (SEQ ID NO: 2) and primer A01 (SEQ ID NO: 3), a set of primer $SO_2$ (SEQ ID NO: 4) and primer A02 (SEQ ID NO: 5), a set of primer $SO_3$ (SEQ ID NO: 6) and primer A03 (SEQ ID NO: 7), and a set of primer $SO_4$ (SEQ ID NO: 8) and primer A04 (SEQ ID NO: 9), i.e., four PCR primer sets, were used. In this connection, as the primers, Easy Oligos (Proligo, Japan) were used.

The conditions in the PCR are shown in Table 2.

TABLE 2

| | Reaction system: | |
|---|---|---|
| 10× | PCR buffer for KOD | 3.0 µL |
| each 2 mmol/L | dNTP mix | 3.0 µL |
| 25 mmol/L | magnesium sulfate | 1.2 µL |
| each 10 µmol/L | PCR primer set | 0.9 µL |
| 1 Unit/µL | KOD-plus- (PCR reaction solution A) | 0.6 µL |
| 10 pg-200 ng | reverse transcribed ss cDNA | 1.0 µL |
| | sterile water | 20.3 µL |
| Total | | 30.0 µL |

[PCR conditions: at 94° C. for 2 minutes, (at 94° C. for 15 seconds, at 55° C. for 30 seconds, and at 68° C. for 1.5 minutes)×35 cycles, and at 68° C. for 1.5 minutes]

As the result of the PCR, the sizes of the DNA fragments amplified with the S01 and A01 primer set, the $SO_2$ and A02 primer set, the $SO_3$ and A03 primer set, and the $SO_4$ and A04 primer set were 798 bp, 951 bp, 551 bp, and 658 bp, respectively. The amplified DNA fragments were purified using ExoSAP-IT (USB) in accordance with a protocol attached thereto. The nucleotide sequence of each purified DNA fragment was conventionally analyzed by a DNA sequencer (ABI PRISM 377, Applied Biosystems) to identify polymorphic sites in the CYP1A2 gene. The PCR primers S01, S02, S03, S04, A01, A02, A03, and A04 were used in the sequence analysis.

The found genetic polymorphisms are summarized in Table 3. In Table 3, the "nucleotide No. in seq." is a number when the starting nucleotide in a known partial nucleotide sequence (Molecular pharmacology, 1990, Vol. 38, p. 644-651) of a beagle CYP1A2 gene is regarded as "1", and the term "known seq." means the known partial nucleotide sequence.

TABLE 3

| Nucleotide No. in seq. | Base in known seq. | Corresponding amino acid in known seq. | EM | PM | Corresponding amino acid in mutated seq. |
|---|---|---|---|---|---|
| 28 | A | Ile | G | A | Val |
| 141 | T | Pro | C | T | Pro |
| 225 | C | Ser | T | C | Ser |
| 300 | G | Leu | C | G | Phe |
| 307 | A | Ile | G | A | Val |
| 309 | T | Ile | G | T | Val |
| 316 | A | Ser | G | G | Gly |
| 325 | A | Met | C | A | Leu |
| 328 | T | Ser | A | T | Thr |
| 363 | C | Ala | G | G | Ala |
| 364 | G | Gly | C | C | Arg |
| 492 | A | Glu | G | A | Glu |
| 538 | C | Leu | A | C | Met |
| 652 | T | Ser | A | T | Asn |

TABLE 3-continued

| Nucleotide No. in seq. | Base in known seq. | Corresponding amino acid in known seq. | EM | PM | Corresponding amino acid in mutated seq. |
|---|---|---|---|---|---|
| 653 | C | Ser | A | C | Asn |
| 664 | T | Leu | G | T | Val |
| 738 | T | Phe | C | T | Phe |
| 795 | T | Ser | T | T/A | Arg |
| 831 | C | Asn | T | T | Asn |
| 982 | C | Gln | A | A | Lys |
| 1087 | C | Arg | C | T | *** : stop codon |
| 1102 | G | Val | G | A | Ile |
| 1206 | C | Gln | C/G | C | Glu |
| 1262 | T | Gly | C/T | T | Gly |
| 1266 | G | Ala | G/A | G | Thr |
| 1269 | C | Gly | T | C | Gly |
| 1273 | A | Thr | G | G | Ala |
| 1421 | A | Asn | A | G | Arg |

Among the SNPs, an SNP in which the base at position 1087 of the known CYP1A2 gene is substituted from C to T, and thereby the corresponding amino acid is changed from arginine to a stop codon was found in the beagle B. It is considered that the SNP may cause a remarkable change in the metabolizing ability of CYP1A2 in the PM-type beagle B.

Example 2

Assay for Identifying Nucleotide Sequence at the 5' Terminal Region of Beagle CYP1A2 Gene by a 5' RACE Method In this example, total RNA isolated from a beagle liver was used as a template, an unidentified nucleotide sequence at the 5' terminal region of beagle CYP1A2 gene was determined by a 5' RACE (5' rapid amplification of cDNA ends) method, and the full-length (from the start codon, methionine to the stop codon) of nucleotide sequence of beagle CYP1A2 cDNA was identified.

Approximately 0.1 g of the liver tissue dissected from the EM-type beagle A in Example 1 was used to extract total RNA by an Invitrogen TRIzol Reagent (Invitrogen) in accordance with a protocol attached thereto.

Approximately 0.1 g of the beagle liver tissue frozen immediately after the dissection was crushed into powder in a mortar, and suspended in 1 mL of Invitrogen TRIzol Reagent (Invitrogen). To the suspension, 0.2 mL of chloroform was added, and the mixture was shaken and centrifuged to collect only the aqueous layer. The aqueous layer was treated by an isopropanol precipitation method to collect RNA as a pellet. The pellet was dissolved in 100 µL of RNase-free water.

To 6.5 µL (10 µg) of the extracted total RNA solution, 1 µL of a 10× DNase I reaction buffer, 1 µL of 1 U/µL DNase I, and 1.5 µL of RNase-free water were added, the mixture was incubated at room temperature for 15 minutes. Then, 1 µL of 25 mmol/L EDTA was further added, and the whole was incubated at 65° C. for 10 minutes.

In accordance with a protocol described in a manual attached to Invitrogen GeneRacer Kit (Invitrogen), a 5' RACE method was carried out using 3 µg of extracted total RNA. Total RNA was treated with calf intestine alkaline phosphatase (CIP). After the CIP treatment, a treatment with tobacco acid pyrophosphatase (TAP) was carried out, whereby a cap structure was removed from capped mRNA to expose the phosphate group at the 5' terminus. To the RNA treated with TAP, GeneRacer RNA Oligo (SEQ ID NO: 19) was ligated by T4 RNA ligase, and treated with Invitrogen SuperScript III RT (Invitrogen) at 50° C. for 60 minutes. The obtained cDNA was used as a template to carry out PCR for amplifying the 5' terminal region with GeneRacer 5'primer (SEQ ID NO: 20) and a gene specific primer (GSP; SEQ ID NO: 21). The reaction conditions are shown in Table 4.

TABLE 4

| Reaction system: | | |
|---|---|---|
| 10 µmol/L | GeneRacer 5' primer | 3.0 µL |
| 10 µmol/L | GSP | 1.0 µL |
|  | template cDNA | 1.0 µL |
| 10× | High Fidelity PCR buffer | 5.0 µL |
| 10 mmol/L | dNTP mix | 1.0 µL |
| 5 U/mL | Platinum Taq High Fidelity | 0.5 µL |
| 50 mmol/L | magnesium sulfate | 2.0 µL |
|  | sterile water | 36.5 µL |
| Total |  | 50.0 µL |

[Reaction conditions: at 94° C. for 2 minutes, (at 94° C. for 30 seconds, and at 70° C. for 5 minutes)×5 cycles, (at 94° C. for 3 seconds, at 65° C. for 30 seconds, and at 68° C. for 5 minutes)×5 cycles, (at 94° C. for 30 seconds, at 60° C. for 30 seconds, and at 68° C. for 5 minutes)×5 cycles, (at 94° C. for 30 seconds, at 55° C. for 30 seconds, and at 68° C. for 5 minutes)×5 cycles, and at 68° C. for 10 minutes]

The PCR product was analyzed by electrophoresis to detect an approximately 250 bp of DNA fragment amplified. The DNA fragment was purified by an Invitorgen S.N.A.P. Gel Purification Kit (Invitrogen). The purified DNA fragment was cloned into vector pCR4-TOPO by an Invitrogen TOPO Cloning Kit.

The sequence of the DNA fragment cloned in vector pCR4-TOPO was analyzed to confirm an overlap with a known partial nucleotide sequence of beagle CYP1A2 (Molecular pharmacology, 1990, Vol. 38, p. 644-651). A consensus sequence between 6 clones analyzed by the 5' RACE method is a nucleotide sequence consisting of nucleotides 1-170 of SEQ ID NO: 22.

From the above obtained overlap of CYP1A2 partial sequence and the known partial nucleotide sequence(s) of the beagle CYP1A2 gene, the full nucleotide sequence of CYP1A2 cDNA in the EM-type beagle A used in Example 1 was determined as the nucleotide sequence of SEQ ID NO: 22 having the open reading frame (ORF) of nucleotides 63-1601.

Further, full nucleotide sequences of CYP1A2 cDNA in nine EM-type beagles were determined. In the beagle A, bases at positions 1305, 1361, 1365, and 1615 of the nucleotide sequence of SEQ ID NO: 22 were heterogeneously C/G, C/T, G/A, and C/T, respectively. In contrast, the corresponding bases in the other beagles were C, C, G, and C, respectively.

From the results, it was clarified that the SNP (isolated in Example 1 and generating a stop codon) at position 1087 of the known partial nucleotide sequence of the CYP1A2 gene corresponds to an SNP in which a base at position 1117 of a beagle CYP1A2 gene (at position 1179 of the nucleotide sequence of SEQ ID NO: 22) is substituted from C to T and an amino acid at position 373 is changed from arginine to a stop codon.

Example 3

SNP in Which a Base at Position 87 of Exon 4 in CYP1A2 Gene is Substituted from C to T To easily detect the SNP in which a base at position 1117 of a beagle CYP1A2 gene is substituted from C to T, a position of the SNP in genomic DNA was examined.

In this example, genome information in an other mammalian CYP1 family was used to predict the position of the SNP of interest, genomic DNA was isolated from beagle leukocytes, PCR was carried out, and nucleotide sequences of genomic DNA including the SNP were determined.

When exons and introns of human CYP1A1 (NCBI accession No. AF253322), human CYP1A2 (NCBI accession No. AF253322), mouse CYP1A1 (NCBI accession No. X01681), mouse CYP1A2 (NCBI accession No. X01682), rat CYP1A2 (NCBI accession No. K02246), and rat CYP1A2 (NCBI accession No. K03241) were prepared, the size of each intron was different among molecules, but the size of each exon was conserved among different species. More particularly, the sizes of exons 1, 2, 3, 4, 5, and 6 in the above mammalian CYP1 family were approximately 830 bp, approximately 120 bp, approximately 89 bp, approximately 123 bp, approximately 86 bp, and approximately 285 bp, respectively. On the basis of this information, the SNP of interest was predicted to be located in exon 4.

To prepare canine genomic DNA, whole blood taken from a beagle using a non-treated injection needle was kept in a sterile vacutainer blood collection tube (Beckton Dickinson, Japan) with EDTA 2K. A GEN-TORUKUN™ (for blood) (Takara Shuzo) was used to extract canine genomic DNA from the whole blood in accordance with a protocol attached thereto.

To amplify a genomic DNA region containing the SNP of interest by using the extracted genomic DNA, PCR was carried out with DNA polymerase KOD-plus- (Toyobo). As a primer set for determining a nucleotide sequence of intron 3, exon 4, and intron 4, a sense primer S05 (SEQ ID NO: 10) was designed on the basis of a sequence within exon 3, and an antisense primer A05 (SEQ ID NO: 11) was designed on the basis of a sequence within exon 5. As the primers, Easy Oligos (Proligo, Japan) were used. The conditions in the PCR are shown in Table 5.

TABLE 5

| Reaction system: | |
|---|---|
| PCR reaction solution A | 8.7 μL |
| 10 pg-200 ng    genomic DNA | 2.0 μL |
|                 sterile water | 19.3 μL |
| Total | 30.0 μL |

[PCR conditions: at 94° C. for 2 minutes, (at 94° C. for 15 seconds, at 56° C. for 30 seconds, and at 68° C. for 30 seconds)×35 cycles, and at 68° C. for 1.5 minutes]

As a result, the size of the DNA fragment amplified with the S05 and A05 primer set was 1380 bp. The amplified DNA fragment was purified using ExoSAP-IT (USB) in accordance with a protocol attached thereto. The nucleotide sequence of the purified DNA fragment was conventionally analyzed by a DNA sequencer (ABI PRISM 377, Applied Biosystems) to identify polymorphic sites in the CYP1A2 gene. The PCR primers $SO_5$, A05, S06 (SEQ ID NO: 12), and A06 (SEQ ID NO: 13) were used in the sequence analysis.

As a result, the nucleotide sequence of SEQ ID NO: 1 was determined. The base T at position 405 of the nucleotide sequence of SEQ ID NO: 1 is the position of the SNP of interest, i.e., position 1117 in a beagle CYP1A2 gene.

The consensus sequences GT and AG exist at both ends of an intron in higher eukaryotic organisms and the CYP1A2 cDNA nucleotide sequence. In accordance with the "GT-AG" rule, the nucleotide sequences of intron 3, exon 4, and intron 4 in CYP1A2 genomic DNA were determined. As a result, it is considered that nucleotides 63-318, nucleotides 319-442, and nucleotides 443-1338 of the nucleotide sequence of SEQ ID NO: 1 are intron 3, exon 4, and intron 4, respectively.

From the above results, it was clarified that the SNP of interest is a substitution from C to T at position 87 of exon 4 of the CYP1A2 gene.

Example 4

SNP Detection by ASP-PCR Method

In this example, to detect the SNP in which the base at position 1117 of the beagle CYP1A2 gene (i.e., at position 87 of exon 4) is substituted from C to T, genomic DNA was isolated from beagle leukocytes, ASP-PCR was carried out, and the presence of the SNP was judged by an agarose gel electrophoresis pattern, in accordance with the following procedures.

Canine genomic DNA was extracted in accordance with the method described in Example 3.

The extracted genomic DNA was used as a template to carry out PCR with DNA polymerase KOD-plus- (Toyobo). As PCR primer sets for an allele-specific reaction, two PCR primer sets, i.e., a set of primer S07wild (SEQ ID NO: 14) and primer A07 (SEQ ID NO: 15) and a set of primer S07mutant (SEQ ID NO: 16) and primer A07, were used. The SNP of interest is recognized at position 19 (C) in the nucleotide sequence of SEQ ID NO: 14 or at position 19 (T) in the nucleotide sequence of SEQ ID NO: 16. As the primers, Easy Oligos (Proligo, Japan) were used. The conditions in the PCR are shown in Table 6.

TABLE 6

| Reaction system: | |
|---|---|
| PCR reaction solution A | 8.7 μL |
| 10 pg-200 ng    genomic DNA | 1.0 μL |
|                 sterile water | 20.3 μL |
| Total | 30.0 μL |

[PCR conditions: at 94° C. for 2 minutes, (at 94° C. for 15 seconds, at 59° C. for 30 seconds, and at 68° C. for 30 seconds)×35 cycles, and at 68° C. for 1.5 minutes]

As a result, the size of the DNA fragment amplified with the S07 wild and A07 primer set was 365 bp, and that amplified with the S07 mutant and A07 primer set was also 365 bp. As the results of the agarose gel electrophoresis, with respect to the SNP from C to T at position 87 of exon 4 in the CYP1A2 gene, when the C allele was present homogeneously, the DNA fragment was amplified only in the case of the PCR with the S07 wild and A07 primer set. When both alleles were present heterogeneously, the DNA fragment was amplified in both cases, i.e., the case with the S07 wild and A07 primer set and the case with the S07 mutant and A07 primer set. When the T allele was present homogeneously, the DNA fragment was amplified only in the case with the S07 mutant and A07 primer set.

Example 5

SNP Detection by a Direct Sequence Method

In this example, to detect the SNP in which the base at position 1117 of the CYP1A2 gene (i.e., at position 87 of exon 4) is substituted from C to T, genomic DNA was isolated from beagle leukocytes, PCR was carried out, and the presence of the SNP was judged by direct sequencing, in accordance with the following procedures.

Canine genomic DNA was extracted in accordance with the method described in Example 3.

The extracted genomic DNA was used as a template to carry out PCR with DNA polymerase KOD-plus- (Toyobo). As the PCR primers, a PCR primer set of primer S05 and primer A07 was used. As the primers, Easy Oligos (Proligo, Japan) were used. The conditions in the PCR are shown in Table 7.

TABLE 7

| Reaction system: | |
|---|---|
| PCR reaction solution A | 8.7 μL |
| 10 pg-200 ng genomic DNA | 1.0 μL |
| sterile water | 20.3 μL |
| Total | 30.0 μL |

[PCR conditions: the same as Example 3]

As a result, the size of the DNA fragment amplified with the S05 and A07 primer set was 752 bp. The amplified DNA fragment was purified using ExoSAP-IT (USB) in accordance with a protocol attached thereto. The nucleotide sequence of the purified DNA fragment was conventionally analyzed by a DNA sequencer (ABI PRISM 377, Applied Biosystems) to identify polymorphic sites in the CYP1A2 gene. The PCR primers S08 (SEQ ID NO: 17) and A08 (SEQ ID NO: 18) were used in the sequence analysis.

As a result, nucleotides at the SNP from C to T at position 1117 of the CYP1A2 gene were identified by a sequence waveform. When the C allele was present homogeneously, only the waveform of C was detected. When both alleles were present heterogeneously, both waveforms of C and T were detected. When the T allele was present homogeneously, only the waveform of T was detected.

Example 6

Analysis of Allele Frequency

In this example, the results obtained in Examples 4 and 5 were used to analyze the allele frequency of the SNP from C to T at position 1117 of the CYP1A2 gene (i.e., at position 87 of exon 4), in accordance with the following procedures.

The results of a gene diagnosis of 65 beagles for the SNP from C to T at position 1117 of the CYP1A2 gene are shown in Table 8.

TABLE 8

| Animal | Number of subject | Genotype C/C | C/T | T/T |
|---|---|---|---|---|
| Beagles | 65 | 25 (0.38) | 29 (0.45) | 11 (0.17) |

In Table 8, "C/C" means a subject homogeneously carrying the C allele in which the base at position of the CYP1A2 gene (i.e., at position 87 of exon 4) is C, "T/T" means a subject homogeneously carrying the T allele in which the base is T, and "C/T" means a subject heterogeneously carrying both alleles. As shown in Table 8, C/C was detected in 25 subjects (38%), C/T was detected in 29 subjects (45%), and T/T was detected in 11 subjects (17%). Each allele frequency was 0.61 (C allele) and 0.39 (T allele).

Example 7

Test for Pharmacokinetics Using Beagles

It is known that a phosphodiesterase IV inhibitor, 4-cyclohexyl-1-ethyl-7-methylpyrido[2,3-d]pyrimidin-2(1H)-one (see Example 7 in Japanese Patent No. 3110765 or WO97/19078; hereinafter referred to as Compound A) is metabolized to 5 different metabolites MM-1 to MM-5 in a beagle. All of the metabolites are compounds in which a hydroxyl group is added, and thus are considered to be products generated by a phase I drug metabolizing reaction. Miyashita et al. reported that beagles were divided into two groups, i.e., a group in which MM-2 was a major metabolite in plasma, and a group in which MM-1 and MM-5 were major metabolites ["The 17th Annual Meeting of the Japanese Society for the Study of Xenobiotics, poster session", Japan, 2002, 20PE-46]

In this example, after oral administration of Compound A, a pharmacokinetics test was carried out, in accordance with the following procedure. In the test, a time course of changes in concentrations of the unreacted compound and metabolites was measured.

Compound A was suspended in 0.5% methyl cellulose solution, and the suspension was orally administered to 10 male beagles (0.3 mg/kg). Blood was collected from each subject after 0.25, 0.5, 1.0, 2.0, 4.0, and 8.0 hours from the administration. Plasma was extracted by liquid-liquid extraction, and then, a time course of changes in concentrations of the unreacted compound and metabolites in plasma was measured according to a simultaneous measurement method (hereinafter referred to as HPLC-FL method) using HPLC and a fluorescence detector.

Conditions in the HPLC-FL method measuring Compound A and metabolites simultaneously are shown in Table 9, and concentration gradients of mobile phases are shown in Table 10.

TABLE 9

| | |
|---|---|
| Column: | COSMOSIL 5PE-MS waters 4.6 (i.d.) × 250 mm |
| Column temperature: | 40° C. |
| Mobile phase: | liquid A; 50 mmol/L acetic acid:acetonitrile = 80:20 |
| | liquid B; 50 mmol/L acetic acid:acetonitrile = 20:80 |
| Flow rate: | 1.0 mL/min |
| Fluorescent detection: | excitation wavelength; 330 nm |
| | fluorescent wavelength; 400 nm |

TABLE 10

| | Time (minute) | | | | | |
|---|---|---|---|---|---|---|
| | 0 | 18 | 30 | 47 | 47.01 | 55 (stop) |
| Mobile phase: liquid A | 90 | 90 | 50 | 50 | 90 | 90 |
| Mobile phase: liquid B | 10 | 10 | 50 | 50 | 10 | 10 |

The beagles for the pharmacokinetics test used in this example were previously selected by carrying out a phenotype analysis. In the pharmacokinetics test, 5 dogs (type I) in which the major metabolite was MM-2, and 5 dogs (type II) in which the major metabolites were MM-1 and MM-5, were used. The time course of changes in concentrations of Compound A and metabolites thereof in plasma are shown in Table 1 (type I) and Table 2 (type II)

As pharmacokinetic parameters, time of maximum observed concentration (Tmax), concentration corresponding to Tmax (Cmax), area under the plasma concentration-time curve from the time of dosing extrapolated to infinity (AUCinf), and terminal half-life (T1/2) were calculated. The results are shown in Table 11.

TABLE 11

| Phenotype analysis | Subject | Tmax (hr) | Cmax (ng/mL) | AUCinf (hr · ng/mL) | T1/2 (hr) |
|---|---|---|---|---|---|
| Type I | MM-1 | 0.5 ± 0.0 | 13.0 ± 5.0 | 17.7 ± 7.4 | 0.6 ± 0.1 |
| (n = 5) | MM-2 | 5.0 ± 0.0 | 106.8 ± 52.9 | 171.5 ± 101.2 | 0.8 ± 0.1 |
| | MM-3 | 0.3 ± 0.1 | 7.9 ± 5.1 | 6.1 ± 4.1 | 0.3 ± 0.0 |
| | MM-4 | 0.3 ± 0.1 | 6.0 ± 2.3 | 4.3 ± 2.0 | 0.4 ± 0.0 |
| | MM-5 | 0.3 ± 0.1 | 9.0 ± 4.9 | 6.7 ± 3.7 | 0.3 ± 0.1 |
| | Compound A | 0.3 ± 0.0 | 3.2 ± 1.5 | 2.8 ± 1.6 | 0.6 ± 0.2 |
| Type II | MM-1 | 1.8 ± 0.4** | 42.0 ± 9.0** | 355.4 ± 83.3** | 4.6 ± 0.6** |
| (n = 5) | MM-2 | 0.6 ± 0.2 | 6.1 ± 1.3** | 15.9 ± 5.9** | 1.3 ± 0.2** |
| | MM-3 | 0.4 ± 0.1 | 3.8 ± 0.7 | 5.4 ± 1.7 | 0.7 ± 0.1** |
| | MM-4 | 0.4 ± 0.1 | 27.5 ± 14.9* | 35.4 ± 19.8** | 0.6 ± 0.1** |
| | MM-5 | 0.7 ± 0.3* | 136.8 ± 48.1** | 366.3 ± 191.5** | 1.1 ± 0.1** |
| | Compound A | 0.3 ± 0.1 | 24.0 ± 14.8* | 27.2 ± 20.2* | 0.8 ± 0.4 |

**$p < 0.01$,
*$p < 0.05$

As to the pharmacokinetic parameters in the unreacted compound, Cmax of type II was 7.5 times that of type I, and AUCinf of type II was 9.7 times that of type I. From the results, it was concluded that type I was type EM and that type II was type PM.

In addition, as the results of the gene diagnosis for the SNP from C to T at position 1117 of the CYP1A2 gene (i.e., at position 87 of exon 4) in Example 6, the EM-type beagles included two subjects of the C/C genotype and three subjects of the C/T genotype, and the PM-type beagles included five subjects of the T/T genotype.

INDUSTRIAL APPLICABILITY

According to the present invention, individual differences in a drug metabolizing ability of dogs used in, for example, a pharmacological effect test or a toxicity test can be detected prior to the test. The present invention can be used in evaluating the pharmacological effects or toxicity of compounds.

Although the present invention has been described with reference to specific embodiments, various changes and modifications obvious to those skilled in the art are possible without departing from the scope of the appended claims.

FREE TEXT IN SEQUENCE LISTING

Figure 1:
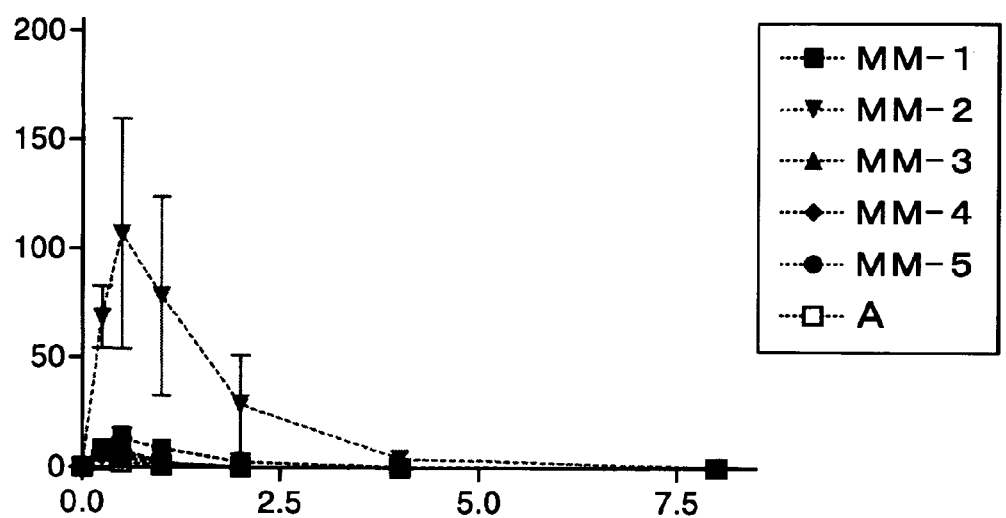
FIG. 1 is a graph showing a time course of changes in concentrations of 4-cyclohexyl-1-ethyl-7-methylpyrido[2,3-d]pyrimidin-2(1H)-one and metabolites thereof in plasma in the type I beagles. The horizontal axis shows a time (hr), and the vertical axis shows a concentration in plasma (ng/mL). The symbol "A" means Compound A.
Figure 2:
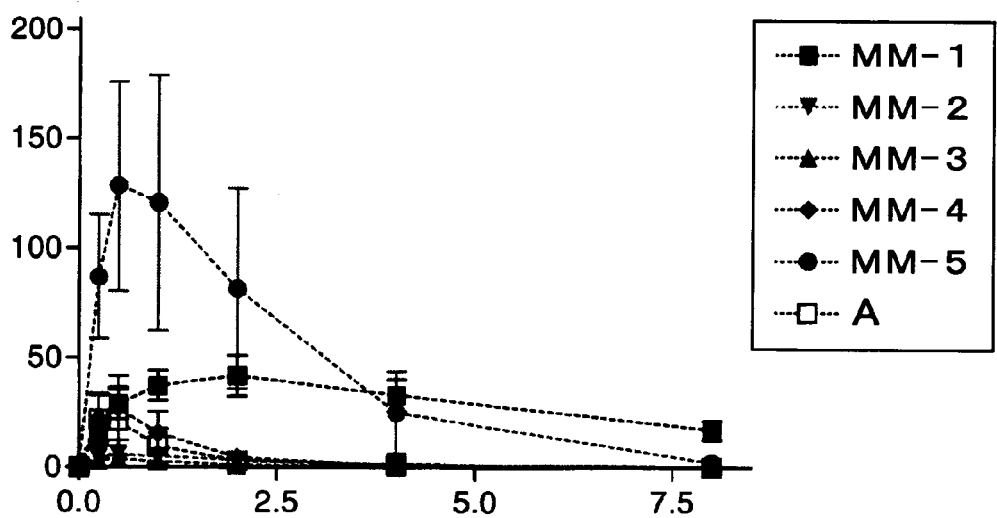
FIG. 2 is a graph showing a time course of changes in concentrations of 4-cyclohexyl-1-ethyl-7-methylpyrido[2,3-d]pyrimidin-2(1H)-one and metabolites thereof in plasma in the type II beagles. The horizontal axis shows a time (hr), and the vertical axis shows a concentration in plasma (ng/mL). The symbol "A" means Compound A.

The nucleotide sequence of SEQ ID NO: 19 is an artificially synthesized GeneRacer RNA Oligo.

The nucleotide sequence of SEQ ID NO: 20 is an artificially synthesized GeneRacer 5' primer.

In the amino acid sequence of SEQ ID NO: 23, the "Xaa" at location 415 stands for Glu or Gln, the "Xaa" at location 433 stands for Gly, the "Xaa" at location 435 stands for Ala or Thr.

The invention claimed is:

1. A method for determining whether a beagle dog is an extensive metabolizer or a poor metabolizer in the rate of drug metabolism, said method comprising:
   preparing a nucleic acid sample from a beagle dog,
   analyzing a base corresponding to a base at position 1179 of the nucleotide sequence of SEQ ID NO: 22,
   determining a CYP1A2 genotype at the base corresponding to the base at position 1179 of the nucleotide sequence of SEQ ID NO: 22, and
   judging the beagle dog with a C/C genotype or a C/T genotype to be an extensive metabolizer and the beagle dog with a T/T genotype to be a poor metabolizer.

2. A method for selecting a beagle dog used in a medicament test, comprising
   determining whether a beagle dog is an extensive metabolizer or a poor metabolizer in the rate of drug metabolism by the method according to claim 1, and
   selecting a beagle dog with a C/C genotype or a C/T genotype as the extensive metabolizer or a beagle dog with a T/T genotype as the poor metabolizer.

3. The method according to claim 2, wherein a beagle dog with the C/C genotype is selected.

4. A method for assaying a pharmacological effect and/or toxicity of a test drug, comprising
   administering a test drug to an extensive metabolizer group or a poor metabolizer group selected by the method According to claim 2, and
   assaying a pharmacological effect and/or toxicity of the test drug.

* * * * *

UNITED STATES PATENT AND TRADEMARK OFFICE
CERTIFICATE OF CORRECTION

| | |
|---|---|
| PATENT NO. | : 7,399,587 B2 |
| APPLICATION NO. | : 10/536809 |
| DATED | : July 15, 2008 |
| INVENTOR(S) | : Daisuke Tenmizu |

Page 1 of 1

It is certified that error appears in the above-identified patent and that said Letters Patent is hereby corrected as shown below:

In claim 1, column 37, line 36, delete "a base corresponding to".

In claim 1, column 37, line 38 - 39, delete "corresponding to the base".

Signed and Sealed this

Thirtieth Day of September, 2008

JON W. DUDAS
*Director of the United States Patent and Trademark Office*